United States Patent
Majima et al.

(10) Patent No.: US 9,446,350 B2
(45) Date of Patent: Sep. 20, 2016

(54) GAS DECOMPOSITION APPARATUS AND METHOD FOR DECOMPOSING GAS

(71) Applicant: SUMITOMO ELECTRIC INDUSTRIES, LTD., Osaka-shi, Osaka (JP)

(72) Inventors: Masatoshi Majima, Osaka (JP); Shinji Inazawa, Osaka (JP); Koji Nitta, Osaka (JP); Masahiro Yamakawa, Osaka (JP); Takayasu Sugihara, Osaka (JP); Yasuhiro Takeda, Osaka (JP); Yoshihiro Akahane, Osaka (JP); Takahiro Imai, Itami (JP)

(73) Assignee: SUMITOMO ELECTRIC INDUSTRIES, LTD., Osaka-shi, Osaka (JP)

(*) Notice: Subject to any disclaimer, the term of this patent is extended or adjusted under 35 U.S.C. 154(b) by 335 days.

(21) Appl. No.: 14/134,874

(22) Filed: Dec. 19, 2013

(65) Prior Publication Data
US 2014/0102913 A1  Apr. 17, 2014

Related U.S. Application Data

(62) Division of application No. 12/936,889, filed as application No. PCT/JP2009/056880 on Apr. 2, 2009, now Pat. No. 8,641,887.

(30) Foreign Application Priority Data

Apr. 9, 2008 (JP) ................................. 2008-101041
Apr. 9, 2008 (JP) ................................. 2008-101042
Apr. 9, 2008 (JP) ................................. 2008-101043

(51) Int. Cl.
*C25B 1/00* (2006.01)
*B01D 53/32* (2006.01)
(Continued)

(52) U.S. Cl.
CPC ............. *B01D 53/326* (2013.01); *A61L 9/012* (2013.01); *A61L 9/014* (2013.01); *A61L 9/16* (2013.01);
(Continued)

(58) Field of Classification Search
None
See application file for complete search history.

(56) References Cited

U.S. PATENT DOCUMENTS 3,616,339 A   10/1971   Marzluff
4,661,422 A   4/1987   Marianowski et al.
(Continued)

FOREIGN PATENT DOCUMENTS

DE   196 21 752 A1   1/1997
JP   S47-015377 A    8/1972
(Continued)

*Primary Examiner* — Arun S Phasge
(74) *Attorney, Agent, or Firm* — Drinker Biddle & Reath LLP

(57) ABSTRACT

[Object] To provide a gas decomposition apparatus and a gas decomposition method in which no safety problems occur in spite of the application of a relatively high voltage between an anode and a cathode for the purpose of decomposing odorous gases of many types.
[Solution] A catalytic electrode layer 6 that contains a catalyst and is porous; a counter electrode layer 7 that forms a pair with the catalytic electrode; and an electrolyte layer 15 that is sandwiched between the catalytic electrode and the counter electrode and has ion conductivity are included. The catalyst is held by the catalytic electrode in the form of being carried by a carrier containing a conductive material or the catalyst is directly carried by the catalytic electrode. A conductive material in the catalytic electrode, the conductive material being in contact with the catalyst, is not a noncovalent carbon material.

10 Claims, 15 Drawing Sheets

(51) Int. Cl.

| | |
|---|---|
| *A61L 9/012* | (2006.01) |
| *A61L 9/014* | (2006.01) |
| *A61L 9/16* | (2006.01) |
| *B01D 53/86* | (2006.01) |
| *B01D 53/88* | (2006.01) |
| *B01D 61/42* | (2006.01) |
| *B01D 69/10* | (2006.01) |
| *B01D 69/12* | (2006.01) |
| *B01D 69/14* | (2006.01) |
| *B01D 71/36* | (2006.01) |
| *B01J 35/00* | (2006.01) |

(52) U.S. Cl.
CPC ........... *B01D 53/32* (2013.01); *B01D 53/8668* (2013.01); *B01D 53/88* (2013.01); *B01D 61/422* (2013.01); *B01D 69/10* (2013.01); *B01D 69/12* (2013.01); *B01D 69/145* (2013.01); *B01D 71/36* (2013.01); *B01J 35/0033* (2013.01); *A61L 2209/213* (2013.01); *A61L 2209/22* (2013.01); *B01D 2251/11* (2013.01); *B01D 2255/102* (2013.01); *B01D 2255/9202* (2013.01); *B01D 2257/7027* (2013.01); *B01D 2257/90* (2013.01)

(56) References Cited

U.S. PATENT DOCUMENTS

| | | | |
|---|---|---|---|
| 5,022,975 | A | 6/1991 | Gordon |
| 6,830,675 | B2 * | 12/2004 | Zur Megede ........ B01D 53/228 204/228.1 |
| 6,896,792 | B2 | 5/2005 | St-Pierre et al. |
| 2004/0247975 | A1 | 12/2004 | Song et al. |
| 2006/0049063 | A1 | 3/2006 | Murphy et al. |
| 2008/0067078 | A1 * | 3/2008 | Kitaori .................. A61L 2/0088 205/746 |

FOREIGN PATENT DOCUMENTS

| | | |
|---|---|---|
| JP | 1-297127 | 11/1989 |
| JP | 6-63343 A | 3/1994 |
| JP | H08-066621 A | 3/1996 |
| JP | 9-143777 | 6/1997 |
| JP | 2701923 | 10/1997 |
| JP | 11-342312 | 12/1999 |
| JP | 2000-140566 A | 5/2000 |
| JP | 2004-174370 | 6/2002 |
| JP | 2005-087586 | 4/2005 |
| JP | 2005-324152 | 11/2005 |
| JP | 2006-032181 A | 2/2006 |
| JP | 2006-169094 | 6/2006 |
| JP | 2006-225218 A | 8/2006 |
| JP | 2007-130557 | 5/2007 |
| JP | 2008-068182 | 3/2008 |

* cited by examiner (a)

(b)

GAS DECOMPOSITION APPARATUS AND METHOD FOR DECOMPOSING GAS

This is a divisional application of copending prior application Ser. No. 12/936,889, having a §371 date of Oct. 7, 2010, which is a national stage filing based on PCT International Application No. PCT/JP2009/056880, filed on Apr. 2, 2009. The copending application Ser. No. 12/936,889 is incorporated by reference herein in its entirety.

TECHNICAL FIELD

The present invention relates to a gas decomposition apparatus and a method for decomposing a gas. Specifically, the present invention relates to a gas decomposition apparatus and a gas decomposition method for decomposing and deodorizing an odorous gas through an electrochemical reaction.

BACKGROUND ART

To decompose odorous components contained in the air by using electrical energy, a deodorization apparatus is proposed in which a hydrogen-ion-conductive electrolyte layer is sandwiched between two electrodes, one (anode) of the electrodes is provided with a gas introduction path, and a voltage is applied between the anode and cathode electrodes to decompose odorous gases (Patent Literature 1). According to this deodorization apparatus, a voltage is applied between the two electrodes so that odorous gases such as acetaldehyde are decomposed and deodorized through an anode reaction. As for this deodorization apparatus, an example in which sulfuric acid is used as an electrolyte and an example in which an ion-conductive resin having hydrogen-ion (proton) conductivity is used as an electrolyte are disclosed. Here, the electrode is formed by applying fine catalytic particles of platinum, ruthenium, iridium, or the like carried by a carbon powder to a porous carbon substrate and firing the resultant porous carbon substrate. Thus, odorous gases such as acetaldehyde, formaldehyde, ethanol, and methanol can be decomposed.

The above-described sulfuric acid is a well known electrolytic solution. The above-described ion-conductive resin is a well known polymeric resin generally referred to as a "perfluorocarbon (PFC) cation exchange polymer". As for PFC polymer membranes in which sulfonic acid groups and carboxylic acid groups are used as ion exchange groups, for example, there is "Nafion" (registered trademark) manufactured by E. I. du Pont de Nemours and Company. Since such PFC polymers lose their ion conductivity without moisture, moisture is necessarily required.

CITATION LIST

Patent Literature

PTL 1: Japanese Patent No. 2701923

SUMMARY OF INVENTION

Technical Problem

In the above-described cases, sulfuric acid or a PFC polymer is used as an electrolyte and a voltage of 0.8 V is applied between the two electrodes. By applying such a voltage between the electrodes, in the above-described gas decomposition apparatus, sulfuric acid or a PFC polymer serving as an electrolyte is kept in a stable state and acetaldehyde, formaldehyde, ethanol, and methanol that are odorous gases can be decomposed. As for ethanol to be decomposed with the deodorization apparatus, the decomposition voltage is 1.3 V. However, as described above, the decomposition of ethanol proceeds under the application of a voltage of 0.8 V. The magnitude of voltage that should be applied between the anode and the cathode to decompose a gas varies depending on the type of the gas to be decomposed and also on the types of electrodes and electrolytes. This has not been completely clarified yet.

Among odorous gases, there are gases of aromatic compounds such as benzene and toluene that have higher decomposition voltages. The decomposition of such aromatic compound odorous gases does not proceed unless a higher voltage is applied between the electrodes. For example, toluene has a decomposition voltage of 2.5 V. However, it is not known what problems are caused by the application of a higher voltage between the electrodes. Fuel cells, which are different from gas decomposition apparatuses in that gas decomposition apparatuses are related to electrical energy input and fuel cells are related to electrical energy output but do share basic chemical reactions with gas decomposition apparatuses, have been actively studied and developed. In contrast, gas decomposition apparatuses have many unknown problems. In most cases, gas decomposition apparatuses are used, for example, in places crowded with many people and indoors where sufficient air circulation is not expected. Accordingly, safety problems that can be caused by the above-described application of high voltage between the electrodes must be meticulously addressed.

Although ethanol has a higher decomposition voltage than water, ethanol is decomposed with the above-described deodorization apparatus with a voltage of 0.8 V between the two electrodes. Thus, this decomposition can be performed without affecting a PFC polymer that necessarily requires moisture or affecting sulfuric acid, which is an aqueous electrolyte. However, when it comes to the above-described gases of aromatic compounds such as benzene and toluene that have higher decomposition voltages, a higher voltage is applied between the electrodes. The higher the applied voltage is, the higher the decomposition rate of odorous components having low decomposition voltages becomes. However, when a voltage equal to or higher than the decomposition voltage of water cannot be applied, the decomposition rate is limited.

Although it cannot be said that PFC polymers are classified as aqueous electrolytes, as described above, PFC polymers lose their ion conductivity without moisture. Thus, when a voltage equal to or higher than the decomposition voltage of water is applied, some problems may be caused. For example, there may be cases where PFC polymers are used and rapid decomposition of odorous gases of many types including aromatic compounds by the application of a voltage equal to or higher than the decomposition voltage of water between the two electrodes is not achieved. For example, when PFC polymers are used as electrolytes, in spite of the necessity of the application of a high voltage for rapid decomposition of aromatic compounds such as toluene, there may be cases where constraints are added, for example, the voltage applied between the anode and the cathode cannot be increased beyond a predetermined value under a long-term use or in dry environments. In addition, when aqueous electrolytes or electrolytes that necessarily require moisture are used, the application of a voltage equal to or higher than the decomposition voltage of water results in decomposition of water using the supplied electrical energy. Thus, energy efficiency is degraded and a decrease in the decomposition rate is unavoidable. Such problems are clearly not desirable for performing rapid deodorization or achieving high energy efficiency.

An object of the present invention is to provide a gas decomposition apparatus with which, under the application of a relatively high voltage between the anode and the cathode, odorous gases of many types can be rapidly decomposed with high energy efficiency without causing safety problems. Here, it is appropriate to make the relatively high voltage to be about 0.8 to 1 V or higher in view of the relationship between the concentration of carbon monoxide and voltage described below (refer to FIG. 2). In this case, in view of the experimental technique, the voltage of about 0.8 to 1 V or higher is the output voltage of a voltage source. That is, the voltage corresponds to the nominal voltage of a battery.

Solution to Problem

A gas decomposition apparatus according to the present invention includes a catalytic electrode that contains a catalyst and is porous; a counter electrode that forms a pair with the catalytic electrode; and an electrolyte that is sandwiched between the catalytic electrode and the counter electrode and has ion conductivity. The catalyst is held by the catalytic electrode in a form of being carried by a carrier containing a conductive material or the catalyst is directly carried by the catalytic electrode. A conductive material in the catalytic electrode, the conductive material being in contact with the catalyst, is not a noncovalent carbon material.

In the above-described configuration, even when a high voltage with which aromatic compound gases are decomposed is applied between the catalytic electrode and the counter electrode, since noncovalent carbon is not in contact with the catalyst, carbon monoxide is not generated. Accordingly, while aromatic compounds are rapidly decomposed, safety can be ensured in that no carbon monoxide is generated. In addition, for example, odorous gases having low decomposition voltages can be decomposed at a high rate by the application of the high voltage. Thus, odorous gases can be decomposed in a short period of time from the initiation of the operation of the gas decomposition apparatus. The noncovalent conductive carbon materials are carbon materials such as carbon black, graphite, and acetylene black (corresponding to the porous carbon substrate and the carbon powder disclosed in Patent Literature 1 described above). In such noncovalent carbon materials, carbon atoms are bonded together through noncovalent bonds. As indicated by the data below, these bonds are broken with use of a voltage source having an output voltage of 0.8 to 1 V or higher in the presence of a catalyst to cause an oxidation reaction to proceed. The "conductive material that is not a noncovalent conductive carbon material" may be any metal material or a covalent carbon material containing an impurity at a high concentration (for example, conductive diamond or the like). The above-described output voltage of a voltage source is not excessively high. To date, cases where such a voltage source is used and a carbon material such as carbon black is used as a catalytic electrode have not been recognized as issues. This is probably due to the following reasons.

(1) To date, the generation of carbon monoxide has probably not been noticed. That is, there has been a possibility of the occurrence of carbon monoxide poisoning; however this has not been recognized.

(2) Such apparatuses are basically not for general purpose use and a small number of apparatuses have been in operation. The application of a nominal voltage does not mean that a voltage that is exactly the nominal voltage is applied to an intended point, and the applied voltage considerably varies in accordance with individual electrochemical system, internal resistance, and the like. Accordingly, in such a small number of apparatuses being in operation, a relatively high voltage has actually not been applied to noncovalent carbon materials used for catalytic electrodes.

The conductive material in the catalytic electrode may be a porous metal and at least a portion of the porous metal may be formed by a plating process. As a result, the proportion of pore portions can be increased and metal plated portions can be made small. Thus, porosity can be selected from among a wide range of values so as to be large. Accordingly, gas to be decomposed can be passed through the catalytic electrode relatively smoothly (at low pressure loss). At this time, the gas does not flow in the form of a laminar flow stagnating in the surface layer of the catalytic electrode but flows in the form of a turbulent flow with gas separating from the surface of the catalytic electrode and new gas being supplied to the surface of the catalytic electrode. Accordingly, by applying a higher voltage, the decomposition can be performed more efficiently. That is, by passing gas through a porous metal entirely formed by a plating process, a gas flow with which the decomposition efficiency can be enhanced under the application of high voltage can be obtained. As a result, while the generation of carbon monoxide is prevented, a higher voltage can be applied to decompose gas components at a higher decomposition rate. In particular, as described below, unlike fuel cells configured to generate electric power by decomposing gas at a high concentration, such a configuration is advantageous for decomposing gas components at a low concentration efficiently.

Whether a porous metal has been formed by a plating process or not can be determined by, for example, observation of sectional texture with an optical microscope and composition analysis of trace components by various solid state spectroscopic techniques. In particular, for example, it is considerably easy to identify that compacting and sintering of powder in which plastic flow due to mechanical processing is generated have not been performed and that casting in which a temperature gradient is unavoidable has not been performed.

The catalyst may be carried by the porous metal through a resin having proton permeability. In this case, an anode that is a catalytic electrode can be prepared by mixing fine catalytic particles or a powder carrying fine catalytic particles with a binder resin having proton permeability, applying the thus-mixed binder resin to the porous metal, and drying the resin. As a result, a gas decomposition apparatus having good electrical or ion conductive continuity to an electrolyte and having a low internal resistance can be produced.

The porous metal may have a porosity of 0.6 or more and 0.98 or less. In this case, a flow can be obtained in which gas components to be decomposed are passed through the catalytic electrode relatively smoothly and separated from the surface of the catalytic electrode and new gas components are supplied to the surface of the catalytic electrode. Accordingly, by applying a higher voltage, a gas flow with which a high decomposition rate is achieved can be provided. As a result, while the generation of carbon monoxide is prevented, the decomposition efficiency of gas components can be enhanced by applying a higher voltage. When the porosity is less than 0.6, a smooth flow is hampered and passing of gas requires a large amount of energy. When the porosity is more than 0.98, the proportion of gas having passed without being subjected to a decomposition reaction increases. Thus, by taking in the gas again and decomposing the gas, the concentration of odorous components in a target space is decreased.

The porous metal may be formed by plating a resin formed by a foaming treatment for forming a large number of bubbles in the resin and a joining pore-formation treatment for joining the bubbles to form pores. In this case, a porous metal can be readily and efficiently obtained with a resin such as urethane or melamine. A porous metal formed by plating a resin formed by a foaming treatment and a joining pore-formation treatment can be made to have small pores and small frames. Accordingly, the above-described flow of separation and supply of new gas in the surface of the catalytic electrode can be locally generated within a micro-area. That is, such turbulent flows having a small size can be locally generated at a high density. As a result, in the catalyst disposed at a high density, the proportion of the catalyst that is in operation at a high efficiency can be increased. Such an effect is considerably advantageous for gas decomposition apparatuses, which are required to efficiently decompose odorous components at a low concentration unlike fuel cells.

When urethane is used as the resin, $400 \leq (x-0.3)y$ can be satisfied where the pore size of a porous metal is defined as x (mm) and the specific surface of the porous metal is defined as y ($m^2/m^3$). In this case, gas flow can be made smooth and a flow with which a high reaction efficiency is achieved can be provided with certainty.

A voltage source with which a voltage of 0.8 V or higher can be applied may be provided. According to experiments performed by the inventors of the present invention, when a voltage source having an output voltage of 0.8 V and a catalytic electrode mainly constituted by a noncovalent carbon material are used, the danger of carbon monoxide needs to be addressed in compliance with strict safety standards. Thus, when a voltage source having an output voltage of 0.8 V or higher is used, the present gas decomposition apparatus can exhibit the advantage of being secure and safe. For example, this is effective when a battery having a nominal voltage of about 0.8 V or higher is used.

The following configuration may be employed: a voltage source with which a voltage of 0.8 V or higher can be applied between the catalytic electrode and the counter electrode is provided; and, in a state in which a voltage of 0.8 V or higher is applied between the catalytic electrode and the counter electrode by using the voltage source, carbon monoxide is not generated. In this case, odorous gases having low decomposition voltages can be decomposed at a high decomposition rate with a voltage of 0.8 V or higher without the possibility of carbon monoxide. Note that, in the state in which a voltage of 0.8 V or higher is applied between the catalytic electrode and the counter electrode by using the voltage source, it is not necessary that 0.8 V or higher is actually applied between the catalytic electrode and the counter electrode. The above-described application of a voltage should be understood to represent, an operation of applying a voltage between the catalytic electrode and the counter electrode by using a voltage source having an output voltage of 0.8 V or higher.

A voltage source with which a voltage of 1.5 V or higher can be applied may be provided. In this case, odorous components of more types can be decomposed without the possibility of the generation of carbon monoxide. In addition, odorous components not having very high decomposition voltages can be decomposed at a high decomposition rate.

The following configuration may be employed: a voltage source with which a voltage of 1.5 V or higher can be applied between the catalytic electrode and the counter electrode is provided; and, in a state in which a voltage of 1.5 V or higher is applied between the catalytic electrode and the counter electrode by using the voltage source, carbon monoxide is not generated. In this case, the decomposition of aromatic compounds having high decomposition voltages can be rapidly performed with a high voltage of 1.5 V or higher. In addition, the decomposition of odorous gases having low decomposition voltages can be performed at a high decomposition rate. Furthermore, to decompose odorous gases having relatively high decomposition voltages more rapidly with certainty, the voltage of the voltage source is preferably set at 2.0 V or higher. Note that, in the state in which a voltage of 1.5 V or higher is applied between the catalytic electrode and the counter electrode by using the voltage source, it is not necessary that 1.5 V or higher is actually applied between the catalytic electrode and the counter electrode. The above-described application of a voltage should be understood to represent an operation of applying a voltage between the catalytic electrode and the counter electrode by using a voltage source having an output voltage of 1.5 V or higher. Such an understanding is common in the present field. In gas decomposition apparatuses, the electrical resistance of the electrolyte and the electrical resistances at the interfaces of the catalytic electrode/electrolyte/counter electrode considerably vary. Even in the same products, these values vary in accordance with production chance and from lot to lot. It is known that, even when a voltage source has a nominal voltage of 1.5 V or higher, the voltage actually applied between the catalytic electrode and the counter electrode by using the voltage source is smaller than the nominal voltage due to various factors.

The conductive material being in contact with the catalyst may be limited to metal and/or conductive diamond. By not using noncovalent carbon fiber or the like and by using a porous metal or a porous material in which a conductive-diamond thin film is formed on a porous substance, the gas decomposition action is achieved and the possibility of the generation of carbon monoxide can be eliminated. Even when noncovalent carbon paper or acetylene black is used, as long as a conductive-diamond thin film is formed on the surface of such a noncovalent material, the generation of carbon monoxide does not occur. Thus, the core material may be a noncovalent carbon material. The conductive diamond may have any form as long as the conductive diamond has conductivity due to an impurity contained therein at a high concentration and bonds between carbon atoms are not noncovalent. A thin film of covalent diamond or a carbon material referred to as a diamond like material that can be substantially seen as being covalent may be employed, the thin film containing an impurity at a high concentration. In particular, conductive diamond doped with boron is preferred.

The carrier may be a conductive-diamond-coated powder that is a powder coated with conductive diamond; or a metal powder. In this case, a reaction in which carriers are used as the carbon source of carbon monoxide does not occur. Thus, aromatic compounds can be decomposed with a high voltage without the generation of carbon monoxide. Here, aromatic compounds are mentioned as gaseous compounds having high decomposition voltages. However, gaseous compounds having high decomposition voltages are not restricted to aromatic compounds and the gaseous compounds are gases having decomposition voltages higher than the decomposition voltage of water and having so high decomposition voltages that the gases are not decomposed unless a voltage at which CO can be generated at a carbon electrode in the presence of a platinum group catalyst is applied.

The catalytic electrode may include a conductive-diamond-coated porous sheet that is a porous material coated with conductive diamond; or a porous metal sheet. In this case, a reaction in which the sheet material of the catalytic electrode is used as the carbon source of carbon monoxide does not occur.

The catalyst may be a platinum group catalyst. In this case, catalytic action excellent in terms of an oxidation reaction can be achieved and gas decomposition can be promoted. Although such a catalyst also has catalytic action for the generation of carbon monoxide, as described above, noncovalent carbon materials are not in contact with the catalyst and hence the generation of carbon monoxide is suppressed. The platinum group catalyst includes one or more of platinum group elements (ruthenium Ru, rhodium Rh, palladium Pd, osmium Os, iridium Ir, and platinum Pt).

The electrolyte may mainly include a uniaxially or biaxially stretched porous polytetrafluoroethylene (PTFE) membrane and a perfluorocarbon ion exchange polymer (PFC polymer) that fills gaps of the porous PTFE membrane and extends from the catalytic electrode to the counter electrode. In this case, while ion conduction between the electrodes is ensured, the PFC polymer can be formed into a thin membrane. As a result, moisture can be readily maintained, the ion conductivity is enhanced, and the electrical resistance is decreased. However, since the PFC polymer is reinforced by the PTFE membrane, the strength of the PFC polymer in the presence of moisture can be enhanced. As for pin holes, the fluorocarbon resin fibers of the PTFE membrane interrupt the pin holes or do not completely interrupt but bend or divert the pin holes. Thus, passage of odorous gas molecules having a large average radius unlike the gas of hydrogen having a small radius can be readily blocked. Accordingly, problems that odorous gases pass by pin holes and hence odorous gases need to be taken in again and decomposed and the decomposition of the odorous gases takes a long period of time can be overcome. The counter electrode may be formed as an electrode layer on which fine metal particles having a catalytic function are carried or an electrode layer not having such a catalytic function. As for the uniaxially or biaxially stretched porous PTFE membrane, for example, a membrane having a pore size of 5 µm or less and a porosity of 50% or more and 95% or less is preferably used.

Biaxially stretched porous PTFE has a structure having a higher density in which fine fibers extend from micro-nodes. The reinforcement of the PFC polymer can be performed with uniaxially stretched porous PTFE. However, since the density of micro-nodes and fibers extending from the micro-nodes is considerably high in biaxially stretched porous PTFE compared with uniaxially stretched porous PTFE, the reinforcement effect of biaxially stretched porous PTFE is considerably high. As a result, to readily maintain moisture, to enhance ion conductivity, and to decrease electrical resistance, the thin membrane can be formed. That is, resistance to a decrease in the strength and to pin holes in the case of a membrane that is thin and moist can be considerably enhanced. As a result, the efficiency can be ensured and the durability can be enhanced.

When the porous PTFE membrane has a porosity of less than 50%, the amount of the PFC polymer that conducts ions is insufficient and the electrical resistance of the electrolyte is increased. Then, to reduce a decrease in the efficiency, the voltage applied between the electrodes is increased, which is not preferred. When the porosity is more than 95%, the reinforcement with the porous PTFE membrane is insufficient. For example, leakage of odorous gases through pin holes increases and the efficiency of deodorization is degraded.

The electrolyte may have a thickness of 50 µm or less. As described above, the reduction in the thickness of the electrolyte constituted by a porous PTFE membrane and a PFC polymer is very preferable in view of achieving a sufficiently high efficiency. When the thickness of the electrolyte is more than 50 µm, the electrical resistance of the electrolyte is increased and the necessary voltage applied needs to be high, which hampers the efficiency, size reduction, weight reduction, and cost effectiveness of the gas decomposition apparatus. However, when the thickness of the electrolyte is less than 100 nm (0.1 µm), pin holes having a large diameter and extending through the solid electrolyte layer are readily formed and leakage of odorous gases tends to occur. In addition, even when reinforcement with a porous PTFE membrane is performed, it is difficult to achieve a sufficiently high durability in the presence of moisture. Accordingly, the lower limit is preferably made to be about 100 nm, more preferably 50 nm, still more preferably 30 nm.

A surface of a fiber of the porous PTFE may be covered with a hydrophilic resin film. PTFE is inherently water repellent and repels water. Accordingly, the integration between PTFE and a PFC polymer having water retentivity is not good, which can cause degradation during usage. However, as described above, by forming a hydrophilic resin film, a large number of micro-nodes and fibers running through the micro-nodes and the PFC polymer are further integrated, that is, the contact resistance between the PTFE and the PFC polymer is increased. Thus, the reinforcing effect provided by the PTFE is considerably enhanced. In addition, a large number of micro-nodes and fibers serve as a water reservoir and can supply moisture to the PFC polymer at the time of the lack of moisture and can absorb water at the time of excessive water. Accordingly, the PFC polymer layer can smoothly exhibit the ion conduction action. As a result, in the state of a thin membrane, a moisture environment is ensured, the ion conductivity is enhanced, and the electrical resistance is decreased. As a result, while a sufficiently high efficiency is ensured, a sufficiently high strength can be ensured.

A method for decomposing a gas according to the present invention includes applying a voltage between a catalytic electrode containing a catalyst and a counter electrode to decompose a gas. In this method, a membrane electrode assembly (MEA) structure in which a conductive material that is in contact with the catalyst in the catalytic electrode does not include noncovalent carbon materials is prepared; and the gas is decomposed by applying the voltage between the catalytic electrode and the counter electrode without generation of carbon monoxide.

According to this method, odorous gases having high decomposition voltages can be rapidly decomposed and safety can be ensured in that no carbon monoxide is generated. To more rapidly decompose such gases including odorous gases having relatively high decomposition voltages with certainty, a higher output voltage is preferably applied.

The gas decomposed may include an aromatic compound gas. In this case, aromatic compound gases such as toluene and benzene can be rapidly decomposed without the generation of carbon monoxide.

Another gas decomposition apparatus according to the present invention includes a catalytic electrode on an oxidation side, the catalytic electrode containing fine catalytic particles; a counter electrode that forms a pair with the catalytic electrode; and an electrolyte sandwiched between the catalytic electrode and the counter electrode, wherein the electrolyte is a nonaqueous electrolyte.

In the above-described configuration, since the membrane electrode assembly (MBA) is formed of, as an electrolyte, a nonaqueous electrolyte that is stable under a voltage higher than the decomposition voltage of water, the voltage applied between the anode and the cathode can be increased and odorous gases of many types can be efficiently decomposed with certainty. Note that, in this case, the output voltage of a voltage source provided for the present gas decomposition apparatus is not necessarily higher than the decomposition voltage of water. This is because the operation can be safely performed with a voltage source having an output voltage lower than the decomposition voltage of water and the nonaqueous electrolyte. In the present gas decomposition apparatus, by increasing the applied voltage irrespective of the decomposition voltage of water, the gas decomposition rate of the gas decomposition apparatus can be increased. The counter electrode layer may be formed as an electrode layer on which fine metal particles having a catalytic function are carried, or an electrode layer not having such fine catalytic particles.

The electrolyte may include (1) an ionic liquid functioning at room temperature or (2) $CsHSO_4$, a molten salt, or a solid oxide electrolyte functioning under heating. In this case, the scope of selection of the electrolyte can be expanded in accordance with, for example, the operation environment, required performance, or required cost effectiveness of the gas decomposition apparatus. For example, since $CsHSO_4$ can function at a low temperature of about 100° C., $CsHSO_4$ is suitable for applications in which cost effectiveness and high decomposition capability are required. Ionic liquids are suitable for applications in which small size, low power, and the like are of higher priority than cost effectiveness. Solid oxide electrolytes, which need to be heated to a high temperature of 300° C. or higher, are suitable for applications in which high decomposition capability, durability, being field-proven, cost effectiveness, and the like are of high priority.

The electrolyte may be a solid membrane containing an ionic liquid. In this case, the structure of the MEA can be simplified. In addition, considerations for leakage of liquid and the like are no longer necessary and safety and reliability can be enhanced. As for such a solid membrane containing an ionic liquid, there is, for example, a polymeric membrane containing an ionic liquid formed by dissolving a resin material in the ionic liquid and polymerizing the resin material.

A voltage source with which a voltage of 1.5 V or higher can be applied may be provided. In this case, whether the decomposition voltages are high or low, odorous gases of many types can be rapidly made harmless.

A voltage source with which a voltage of 1.5 V or higher can be applied between the catalytic electrode and the counter electrode may be provided. In this case, odorous gases such as aromatic compounds can be rapidly decomposed. In particular, when rapid decomposition of odorous gases is required, a voltage source of 2.0 V or higher is desirably provided. Note that, in the state in which a voltage of 1.5 V or higher is applied between the catalytic electrode and the counter electrode by using the voltage source, it is not necessary that 1.5 V or higher is actually applied between the catalytic electrode and the counter electrode. The above-described application of a voltage should be understood to represent an operation of applying a voltage between the catalytic electrode and the counter electrode by using a voltage source having an output voltage of 1.5 V or higher. Such an understanding is common in the present field. In gas decomposition apparatuses, the electrical resistance of the electrolyte and the electrical resistances at the interfaces of the catalytic electrode/electrolyte/counter electrode considerably vary. Even in the same products, these values vary in accordance with production chance and from lot to lot. It is known that, even when a voltage source has a nominal voltage of 1.5 V or higher, the voltage actually applied between the catalytic electrode and the counter electrode by using the voltage source is often smaller than the nominal voltage due to various factors.

The following configuration may be employed: a conductive material in the catalytic electrode, the conductive material being in contact with the fine catalytic particles is not a noncovalent carbon material. In this case, when an external voltage is applied in the state in which the temperature is increased, the generation of gases such as carbon monoxide due to the decomposition of noncovalent carbon can be prevented.

A conductive material that is one of main constituent materials of the catalytic electrode and is in contact with the fine catalytic particles so that electrons generated by a gas decomposition reaction are conducted through the conductive material may be limited to metal and/or conductive diamond. In this case, odorous component gases can be efficiently decomposed with an existing material without the possibility of the generation of carbon monoxide.

Still another gas decomposition apparatus according to the present invention includes a decomposition-side electrode being a porous electrode into which gas containing a component to be decomposed is introduced; a counter electrode that forms a pair with the decomposition-side electrode and is porous; and an electrolyte sandwiched between the decomposition-side electrode and the counter electrode, wherein a portion of the decomposition-side electrode, the portion being in contact with the electrolyte, is composed of a material that is inert to water.

In the above-described configuration, even when a voltage equal to or higher than the decomposition voltage of water (1.23 V) is applied between the decomposition-side electrode and the counter electrode, water is not decomposed within the tolerance range (within the range of the window). Accordingly, when gases to be decomposed having high decomposition voltages are decomposed, by applying a voltage equal to or higher than the decomposition voltage of water (1.23 V), the gases can be decomposed with a high energy efficiency. In addition, gases having low decomposition voltages can be rapidly decomposed with a high energy efficiency at a high decomposition rate according to the magnitude of the applied voltage.

Note that, in this case, the output voltage of a voltage source provided for the present gas decomposition apparatus is not necessarily higher than the decomposition voltage of water. This is because the operation can be safely performed with a voltage source having an output voltage lower than the decomposition voltage of water and the material that is inert to water. In such a gas decomposition apparatus, by increasing the applied voltage irrespective of the decomposition voltage of water, the gas decomposition rate of the gas decomposition apparatus can be increased.

Such a material that is inert to water does not have high catalytic activity compared with platinum group catalysts. However, supplied electrical energy is not used for the decomposition of water and hence the energy efficiency can be enhanced and a practically feasible decomposition rate can be achieved. When an aqueous electrolyte or a perfluorocarbon electrolyte is used as the electrolyte, a situation in which the lack of water is caused by the electrolysis of water and target gases cannot be decomposed can be avoided. Thus, the lasting stability of the decomposition operation can be achieved. It is not necessary that the entirety of the decomposition-side electrode is composed of a material that is inert to water. It will suffice that a portion (such as a surface layer) of the decomposition-side electrode being in contact with the electrolyte is composed of a material that is inert to water.

A voltage source with which a voltage of 1.23 V or higher can be applied may be provided. In this case, gases having low decomposition voltages can be rapidly made harmless and aromatic compounds and the like having high decomposition voltages can be decomposed.

The following configuration may be employed: a voltage source with which a voltage of 1.23 V or higher can be applied is provided; the electrolyte is an electrolyte containing water; and, in a state in which a voltage of 1.23 V or higher is applied between the decomposition-side electrode and the counter electrode by using the voltage source, the water in the electrolyte is not decomposed. In this case, aromatic compounds and the like having high decomposition voltages can be decomposed with a high voltage, high energy efficiency, and lasting stability.

Note that, in the state in which a voltage of 1.23 V or higher is applied between the catalytic electrode and the counter electrode by using the voltage source, it is not necessary that 1.23 V or higher is actually applied between the catalytic electrode and the counter electrode. The above-described application of a voltage should be understood to represent an operation of applying a voltage between the catalytic electrode and the counter electrode by using a voltage source having an output voltage of 1.23 V or higher. Such an understanding is common in the present field. In gas decomposition apparatuses, the electrical resistance of the electrolyte and the electrical resistances at the interfaces of the catalytic electrode/electrolyte/counter electrode considerably vary. Even in the same products, these values vary in accordance with production chance and from lot to lot. Even when a voltage source has a nominal voltage of 1.23 V or higher, the voltage actually applied between the catalytic electrode and the counter electrode by using the voltage source is often smaller than the nominal voltage due to various factors.

The decomposition-side electrode may be covered with conductive diamond or may contain any one of a conductive oxide, a conductive nitride, and a conductive sulfide. In this case, a decomposition-side electrode that is inert to water can be obtained.

The decomposition-side electrode may contain $Ti_4O_7$ or $PbO_2$. In this case, a decomposition-side electrode that is inert to water can be obtained by using such an available specific material, as well as by the technique of covering the decomposition-side electrode with conductive diamond.

The decomposition-side electrode may include a porous sheet covered with conductive diamond on which $Ti_4O_7$ powder and/or $PbO_2$ powder is held. In this case, the decomposition of odorous components can be promoted.

Another method for decomposing a gas according to the present invention includes applying a voltage between a decomposition-side electrode and a counter electrode that sandwich an electrolyte therebetween, and introducing gas containing a component to be decomposed into the decomposition-side electrode to decompose the component. In this method, the decomposition-side electrode contains a material that is inert to water and the electrolyte contains an electrolyte containing water; and a voltage of 1.23 V or higher is applied between the decomposition-side electrode and the counter electrode so that the component is decomposed without decomposing the water in the electrolyte.

According to the above-described method, since target gases are decomposed with a voltage of 1.23 V or higher, gases having low decomposition voltages can be decomposed at a high decomposition rate and gases having high decomposition voltages can be decomposed at a practical decomposition rate. In both cases, the decomposition of water does not occur and hence energy efficiency can be enhanced.

Advantageous Effects of Invention

According to a gas decomposition apparatus and a gas decomposition method according to the present invention, under the application of a relatively high voltage between the anode and the cathode, odorous gases of many types can be rapidly decomposed with high energy efficiency while safety can be ensured in that no carbon monoxide is generated.

DESCRIPTION OF EMBODIMENTS

First Embodiment

Figure 1:
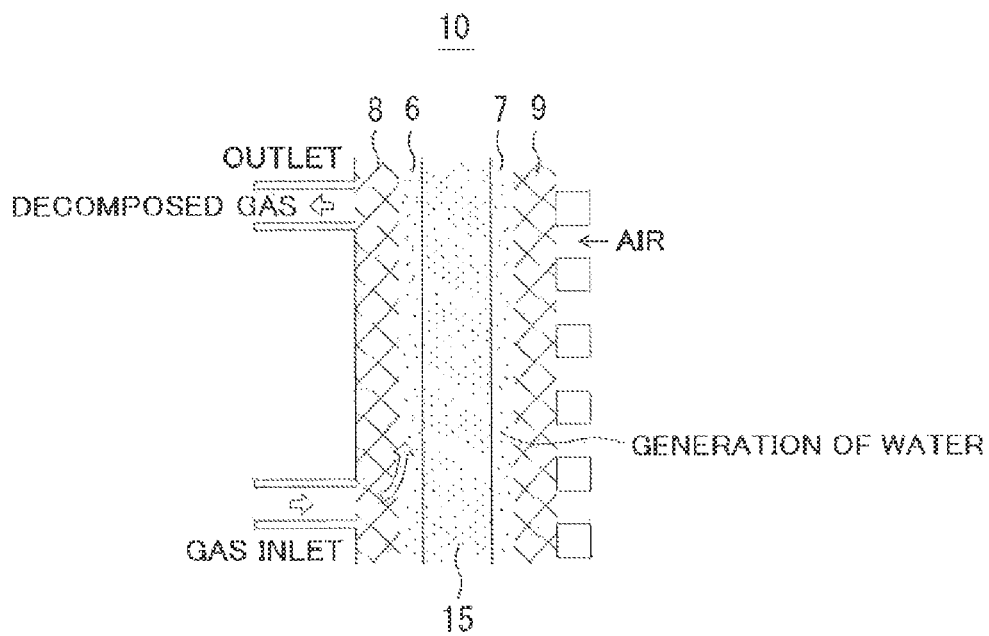
FIG. 1 is a sectional view of a gas decomposition apparatus according to a first embodiment of the present invention.

FIG. 1 illustrates a gas decomposition apparatus 10 according to a first embodiment of the present invention. In the gas decomposition apparatus 10, a catalytic electrode layer 6 and a counter electrode layer 7 are disposed with a solid electrolyte layer 15 therebetween. Both the catalytic electrode layer 6 and the counter electrode layer 7 contain line catalytic particles of platinum or the like. Such fine catalytic particles may be contained in the form of being carried by a conductive powder (carriers) in the two electrodes or may be, without carriers, made to directly adhere to (be carried by) electrode sheets by plating or the like, the electrode sheets serving as conductive bases forming the electrodes. A porous gas-diffusion layer 8 through which an odorous gas to be decomposed is introduced and from which the odorous gas having been subjected to a decomposition reaction (anode reaction or oxidation reaction) is discharged is provided for the catalytic electrode layer 6. The porous gas-diffusion layer 8 is preferably composed of a conductive material such as CELMET (registered trademark), which is a porous metal manufactured by Sumitomo Electric Industries, Ltd. A porous gas-diffusion layer 9 composed of CELMET or the like is also provided for the counter electrode layer 7 for the purpose of introducing air to provide oxygen for a cathode reaction and discharging water generated by the cathode reaction (reduction reaction).

Figure 2:
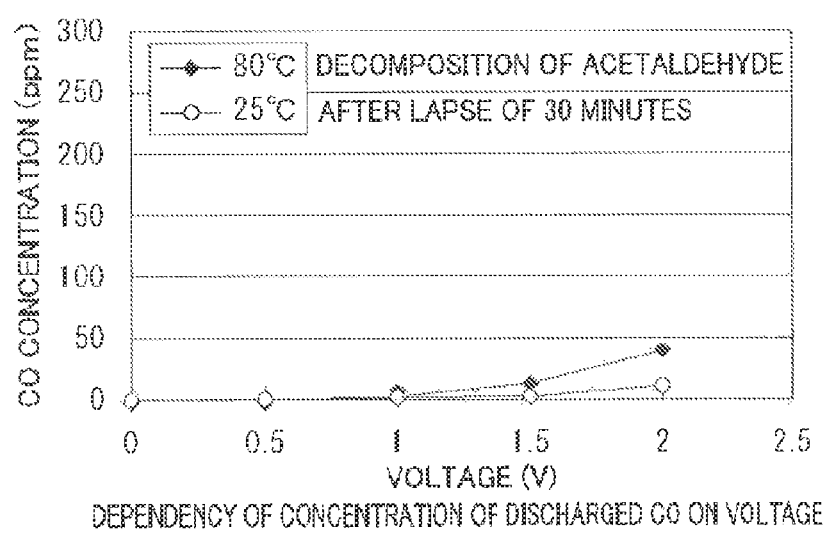
FIG. 2 is a graph illustrating the influence of applied voltage and temperature on the generation of carbon monoxide when an existing gas decomposition apparatus is used.

Before the structure of a gas decomposition apparatus according to the present invention is described, experimental results serving as the reason why the structure is employed will be described. FIG. 2 is a graph illustrating experimental results for an existing gas decomposition apparatus. This gas decomposition apparatus included platinum serving as a catalyst, carbon black serving as catalyst carriers, carbon paper serving as the conductive base or the porous sheet of a catalytic electrode, and Nafion (PFC polymer) serving as an electrolyte. The test environment was at room temperature and at a room humidity of about 30% to 50%. The higher the temperature and the humidity become, the more carbon monoxide is generated. The test was performed with a cell measuring 3.5 cm per side in terms of the area of electrodes by introducing a gas at a predetermined concentration into a 3 L tetra bag, circulating the gas in the cell at 0.5 L/min with a metering pump, and appropriately terminating the circulation and measuring the concentration of gas such as CO at the outlet side of the cell. As described above, both the carbon black serving as the catalyst carriers and the carbon paper serving as the electrode sheet were noncovalent. FIG. 2 shows that the application of a voltage of 1.5 V between the two electrodes at 80° C. resulted in the generation of carbon monoxide after at least 30 minutes had elapsed. In addition, the application of a voltage of 2 V at room temperature resulted in the generation of carbon monoxide after at least 30 minutes had elapsed. Sources of the generation of carbon monoxide other than the air are the above-described carbon black and carbon paper, which are noncovalent carbon materials. Decomposition of gas that is not limited to hydrocarbons occurs at a position where fine catalytic particles 11, the catalytic electrode layer 6 (catalyst carriers 21 in the case of using catalyst carriers), and the electrolyte layer 15 are in contact with each other. Carbon monoxide is generated when noncovalent carbon black or noncovalent carbon paper is present in such a contact position.

Figure 3:
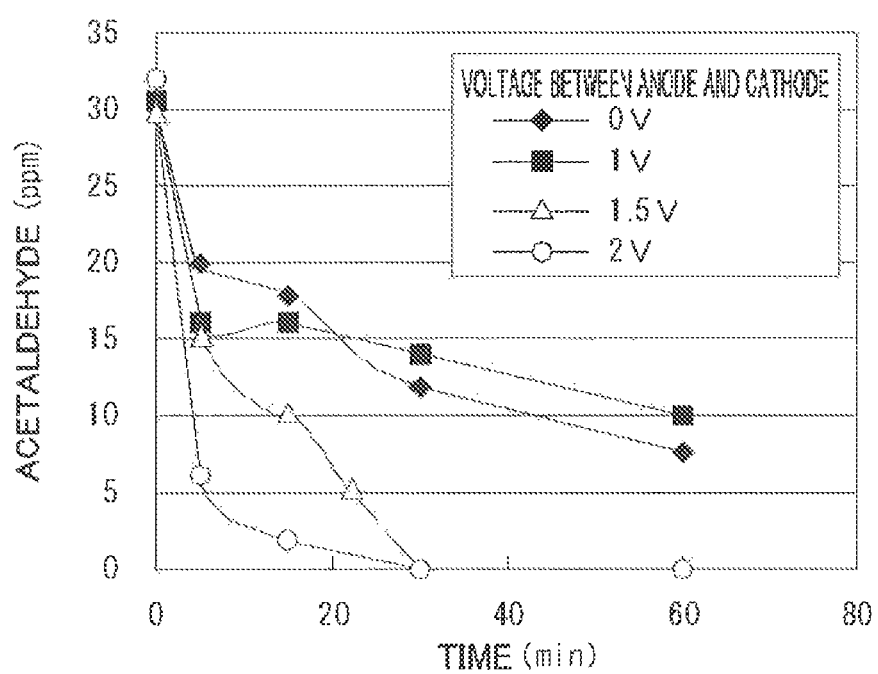
FIG. 3 is a graph, illustrating the influence of applied voltage on the decomposition rate of acetaldehyde decomposed with the same gas decomposition apparatus as in the experiments in conjunction with FIG. 2.

FIG. 3 is a graph illustrating the influence of the voltage between the anode and the cathode on the decomposition rate of acetaldehyde decomposed with the gas decomposition apparatus described in conjunction with FIG. 2. FIG. 3 indicates that, as the voltage between the two electrodes increases from 1 V to 1.5 V to 2 V, the concentration of acetaldehyde decreases in a shorter time. Accordingly, when a gas other than an aromatic compound gas is decomposed, the gas having a low decomposition voltage compared with aromatic compound gases, the decomposition rate can be increased by increasing the voltage applied between the two electrodes.

Features of the Present Embodiment

The gas decomposition apparatus 10 according to the present invention has a feature that noncovalent carbon materials such as carbon fiber sheets and carbon black are not used as conductive materials with which fine catalytic particles are in contact. In particular, the present embodiment has a feature that a porous conductive sheet forming the catalytic electrode layer 6 is formed of a metal and, when carriers are made to carry a catalyst, the carriers are formed of a metal. Since such a porous metal conductive sheet is porous, fine catalytic particles can be directly carried by the sheet and it is not necessary to prepare carriers such as a powder. However, fine catalytic particles may be carried by carriers and the carriers may be held by the porous sheet of the electrode. The term "powder" is a name that identifies the classification of a product. However, other than such a classification name for products, the term "powder" also refers to particles having a considerably larger size than fine catalytic particles. The electrolyte may be any electrolyte, for example, a PFC polymer that functions at room temperature such as Nafion or any nonaqueous electrolyte such as an ionic liquid. As for such nonaqueous electrolytes, other than ionic liquids, the following electrolytes that function under heating may be used: $CsHSO_4$, phosphoric acid-based proton conductors such as $(NH_4)_2K_{1-x}PO_3$, molten salts, and solid oxide electrolytes. Alternatively, phosphoric acid may be used as the electrolyte. Thus, the scope of selection of the electrolyte can be expanded in accordance with, for example, the operation environment, required performance, or required cost effectiveness of the gas decomposition apparatus. For example, since $CsHSO_4$ can function at a low temperature of about 100° C., $CsHSO_4$ is suitable for applications in which cost effectiveness and high decomposition capability are required. Ionic liquids are suitable for applications in which small size, low power, and the like are of higher priority than cost effectiveness. Solid oxide electrolytes, which need to be heated to a high temperature of 300° C. or higher, are suitable for applications in which high decomposition capability, durability, being field-proven, cost effectiveness, and the like are of high priority.

Figure 4:
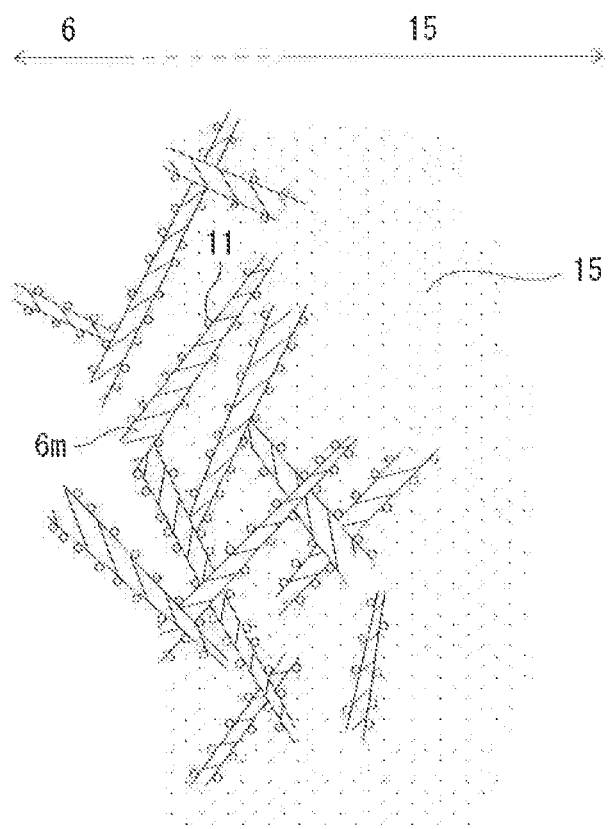
FIG. 4 is a sectional view illustrating a region near the interface between the catalytic electrode and the electrolyte of a gas decomposition apparatus according to the first embodiment of the present invention.

A catalytic electrode containing fine catalytic particles may employ the following structures. (1) As illustrated in FIG. 4, fine catalytic particles 11 are directly carried on the surface of a porous metal sheet 6m described above. The metal sheet 6m may be any porous metal such as metal fiber obtained by processing nickel fine wires, niobium fine wires, titanium fine wires, or the like into a fibrous form; a porous metal material such, as CELMET; or a metal sinter obtained by sintering a metal powder.

Figure 5:
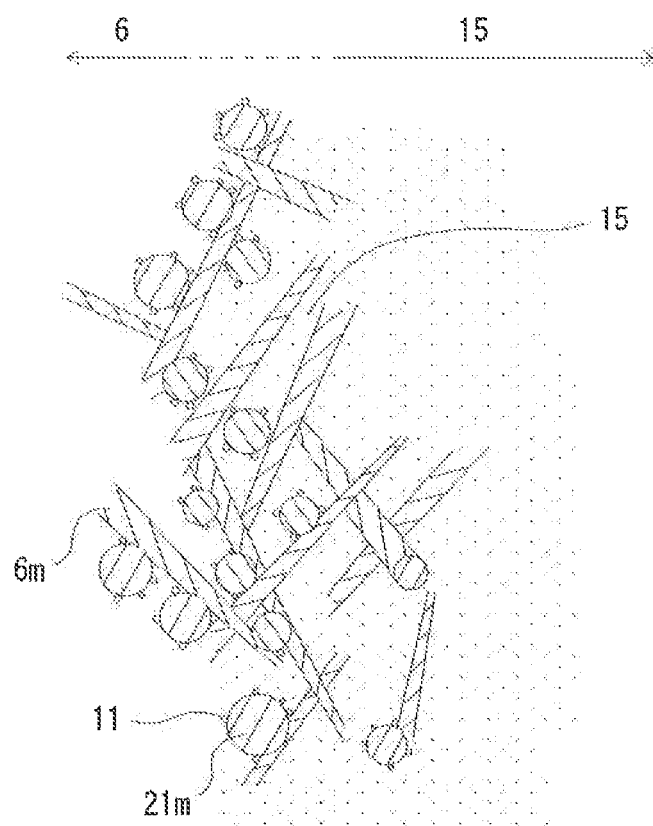
FIG. 5 is a sectional view illustrating a region near the interface between the catalytic electrode and the electrolyte of a gas decomposition apparatus according to a modification of the gas decomposition apparatus illustrated in FIG. 4.

(2) As illustrated in FIG. 5, a structure in which a conductive metal powder 21m of nickel, cobalt, silver, molybdenum, or the Like on the surfaces of which the fine catalytic particles 11 are carried is dispersed in a binder resin having proton permeability and provided on the surface of the porous metal sheet 6m can be employed.

As for the catalytic electrode layer 6 in (1) above (although "the counter electrode layer 7 containing a catalyst" is also included, the description thereof is omitted for the sake of simplicity), for example, in the state in which the porous metal sheet 6m is immersed in a solution containing metal ions forming the fine catalytic particles 11, the metal ions are reduced with a reducing agent to precipitate the fine catalytic particles 11 composed of the metal onto the porous metal sheet 6m. As described above, when a porous metal sheet is used as a conductive base, fine catalytic particles also precipitate onto the inner surfaces of many pores. In such precipitation, fine catalytic particles are carried by the porous metal sheet 6m.

A catalytic electrode layer in (2) above is formed as follows. For example, the metal powder 21m of nickel, silver, or the like is prepared. In the same manner as described above, the metal powder 21m is then immersed in a solution containing metal ions forming fine catalytic particles and a catalyst is precipitated in the form of fine particles onto the surfaces of the metal powder by using a reducing agent. Such a catalyst-carrying metal powder 21m, fine catalytic particles 11 is mixed with a solution of a binder resin having ion permeability to prepare a coating solution. The coating solution is then applied to a surface of the porous metal sheet 6m and dried to form a binder resin membrane in which the above-described carrier metal powder 21m, fine catalytic particles 11 is dispersed. In the catalytic electrode layer of (2) above, as described above, porous metal fiber such as nickel fiber, niobium fiber, or titanium fine wires; a porous metal material such as CELMET; a metal sinter; or the like is used as a conductive base. In addition, the binder resin membrane is stacked so as to be in contact with the electrolyte.

In such a stack, while the contact between the fine catalytic particles and odorous components is maintained with the porous conductive base, the catalyst-carrying powder is dispersed in a membrane composed of a binder resin having proton permeability, and the membrane is sandwiched between the conductive base and the solid electrolyte. Accordingly, for example, removal of the line catalytic particles is suppressed and hence the catalytic action can be maintained for a longer period of time.

As for the fine catalytic particles, a platinum group element such as platinum, ruthenium, palladium, iridium, or osmium; an iron group metal such as iron, cobalt, or nickel; or a noble metal such as vanadium, manganese, silver, or gold is preferably used. In particular, platinum group elements are preferred because they exert an excellent catalytic action on an oxidation reaction. Alternatively, to enhance a special function, fine catalytic particles composed of an alloy of such metals may be used. For example, to enhance a catalyst-poison resistance serving as a catalytic function, an alloy in which the mass ratio of platinum to palladium Pt/Pd satisfies about 7/3 to 9/1 may be used.

In the gas decomposition apparatus 10, by applying a voltage of, for example, 1.5 to 2 V or higher to the two electrodes, aromatic compound gases can be rapidly decomposed without the possibility of the generation of carbon monoxide. In addition, by applying the above-described high voltage, not only aromatic compounds but also odorous gases having low decomposition voltages such as acetaldehyde and ethanol can be rapidly decomposed.

Second Embodiment

Figure 6:
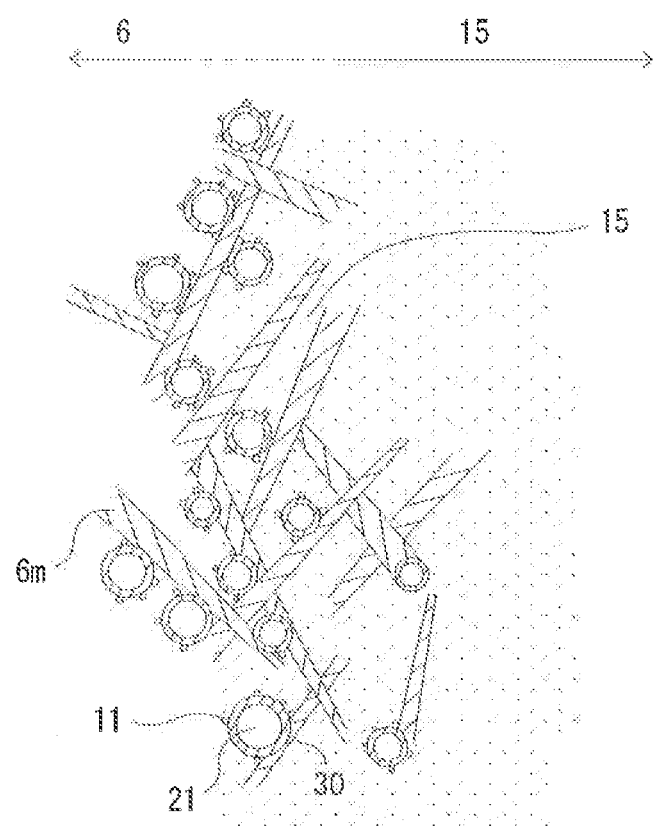
FIG. 6 illustrates an electrolyte-side portion of the catalytic electrode of a gas decomposition apparatus according to a second embodiment of the present invention.

FIG. 6 illustrates an electrolyte-side portion of a catalytic electrode of a gas decomposition apparatus according to a second embodiment of the present invention. The present embodiment has a feature that carriers carrying a fine catalytic particles 11 are coated with a thin film of conductive diamond 30 and a metal (porous metal sheet 6m) is used as a porous sheet for the catalytic electrode. Cores of the carriers 21 may be any powder and a metal, an insulating material, or a noncovalent carbon material such as carbon black may be used. In the present embodiment, the configuration of the gas decomposition apparatus 10 illustrated in FIG. 1 is employed and the porous metal 6m is used as a sheet material of the catalytic electrode layer 6. The porous metal sheet 6m serving as a sheet material of the catalytic electrode layer 6 may be any porous metal sheet such as metal fiber obtained by processing nickel fine wires, niobium fine wires, or the like into a fibrous form; a porous metal material such as CELMET; or a metal sinter obtained by sintering a metal powder. The electrolyte may be a PFC polymer or any nonaqueous electrolyte such as an ionic liquid. The catalyst is preferably a platinum group catalyst in view of promoting decomposition reactions of gases. However, another catalyst may be used.

As illustrated in FIG. 6, as for the catalyst of the catalytic electrode layer 6, carriers that are formed by coating the powder (cores) 21 with the thin film(s) of the conductive diamond 30 and that are made to carry the fine catalytic particles 11 are used. That is, a structure in which the above-described catalyst-carrying carriers 21, 30, 11 are dispersed in a binder resin having proton permeability and provided on a surface of the porous metal sheet 6m can be employed. The powder 21 may be a metal powder, an insulating powder, or a conductive carbon powder of carbon black, acetylene black, or the like. When the cores are composed of an insulating material, conductivity can be provided by the thin film(s) of the conductive diamond 30 covering the powder 21. As for the conductive diamond 30, covalently bonded carbon atoms themselves do not have conductivity. However, by making such a material to contain an impurity such as boron at a high concentration, the resultant conductive diamond 30 can have conductivity. The conductive diamond 30 can be formed in the form of thin films on the powder 21 that serve as cores by a microwave plasma chemical vapor deposition (CVD) technique or the like while the powder 21 is suspended. At this time, doping with a p-type impurity such as boron at a high concentration is performed to impart conductivity.

Carriers that carry line catalytic particles are formed in the following manner. For example, (i) a metal powder of nickel, silver, or the like, (ii) a powder in which conductive-diamond surface layers are formed on a metal powder, (iii) a composite carbon powder in which conductive-diamond thin films are formed on the surfaces of a conductive carbon powder such as carbon black, or (iv) a powder in which conductive-diamond thin films are formed on an insulating powder is prepared. Such a powder 21, 30, 11 is then immersed in a solution containing metal ions forming fine catalytic particles and the metal is precipitated in the form of fine particles onto the surfaces of the powder 21, 30 by using a reducing agent (refer to FIG. 6). The catalyst-carrying powder 21, 30, 11 is mixed with a solution of a binder resin having ion permeability to prepare a coating solution. The coating solution is then applied to a surface of the porous metal sheet 6m and dried to form a binder resin membrane in which the carrier powder is dispersed. In the catalytic electrode layer 6, the porous metal sheet 6m is used as a conductive base. In addition, the binder resin membrane is stacked so as to be in contact with the electrolyte. In such a stack, while the contact between the fine catalytic particles and odorous components is maintained with the porous metal sheet 6m, the catalyst-carrying powder 21, 30, 11 is dispersed in the membrane composed of a binder resin having proton permeability, and the membrane is sandwiched between the porous metal, sheet 6m and the solid electrolyte. Accordingly, for example, removal of the fine catalytic particles is suppressed and hence the catalytic action can be maintained for a longer period of time.

In the gas decomposition apparatus according to the present embodiment, the powder 21 is covered with the thin film(s) of the conductive diamond 30 and the porous metal sheet 6m is used for the catalytic electrode layer 6. Thus, the fine catalytic particles 11 are not in contact with a noncovalent carbon material such as carbon black or carbon fiber. Therefore, by applying a high voltage of 1.5 to 2 V or higher between the anode and the cathode, aromatic compounds can be rapidly decomposed without the possibility of the generation of carbon monoxide. In addition, gases having low decomposition voltages can be decomposed at a high decomposition rate.

Third Embodiment

Figure 7:
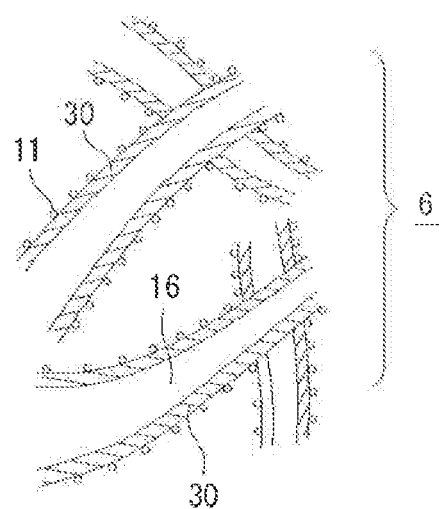
FIG. 7 illustrates the catalytic electrode of a gas decomposition apparatus according to a third embodiment of the present invention.

FIG. 7 illustrates the catalytic electrode of a gas decomposition apparatus according to a third embodiment of the present invention. The present embodiment has a feature that the catalytic electrode layer 6 is produced using a porous sheet 16 covered with a thin film of conductive diamond 30. The core material of the porous sheet 16 of the catalytic electrode layer 6 may be any material and a metal, an insulating material, noncovalent carbon fiber, or the like may be used. In the present embodiment, the configuration of the gas decomposition apparatus 10 illustrated in FIG. 1 is employed. The electrolyte may be a PFC polymer or arty nonaqueous electrolyte such as an ionic liquid. The catalyst is preferably a platinum group catalyst in view of promoting decomposition reactions of gases. However, another catalyst may be used.

When the porous sheet covered with the thin film(s) of the conductive diamond 30 is a fibrous sheet, it is preferred that the thin film(s) of the conductive diamond 30 be formed on threads and the threads be then woven together. In the case of a porous metal material such as CELMET, it is preferred that the porous metal material be placed in a plasma CVD chamber, irradiated with carbon plasma, and doped with an impurity at a high concentration to form the thin film(s) of the conductive diamond 30 both on an outer surface and an inner surface of the porous material. A porous insulating material can be treated in the same manner. A porous sheet prepared in the above-described manner and illustrated in FIG. 7 is used to form the catalytic electrode layer 6. At this time, a structure below is employed depending on whether carriers are used or not.

(1) As illustrated in FIG. 7, the porous sheet 16, 30 included in the catalytic electrode layer 6 is made to directly carry the fine catalytic particles 11.

Figure 8:
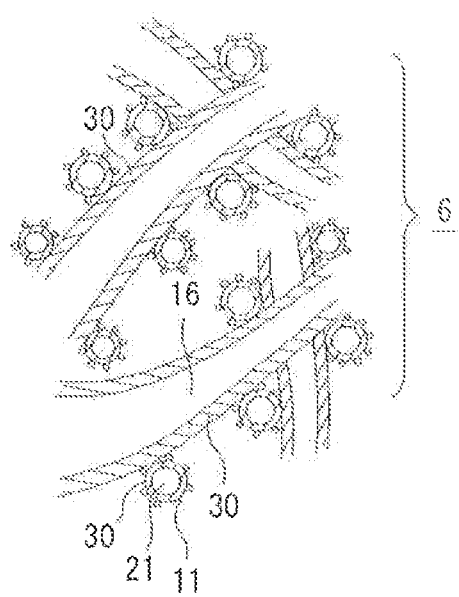
FIG. 8 illustrates an example in which carriers are used in the catalytic-electrode of a gas decomposition apparatus according to the third embodiment of the present invention.

(2) Alternatively, FIG. 8 illustrates an example in which the porous sheet 16, 30 is made to hold carriers 21, 30, 11 carrying the fine catalytic particles 11. The catalyst earners 21, 30, 11 include the core materials of the carriers 21 covered with the thin film(s) of the conductive diamond 30 and hence are the same as those in the second embodiment. As for the carriers carrying the fine catalytic particles 11, other than the configuration illustrated in FIG. 8, the metal powder 21m may be made to carry the fine catalytic particles 11 as illustrated in FIG. 5 according to the first embodiment and the resultant metal powder 21m may be held by the porous sheet 16, 30 illustrated in FIG. 7.

In the gas decomposition apparatus according to the present embodiment, the porous sheet 16, 30 covered with the thin film(s) of the conductive diamond 30 is used for the catalytic electrode layer 6 and the porous sheet 16, 30 directly carries the fine catalytic particles 11. Alternatively, when carriers for fine catalytic particles are used, a metal powder (first embodiment) or carriers in which a powder is covered with the thin film(s) of the conductive diamond 30 (second embodiment) are used as the carriers. Thus, the fine catalytic particles 11 are not in contact with noncovalent carbon materials such as carbon black and carbon fiber. As a result, by applying a high voltage of 1.5 to 2 V or higher between the anode and the cathode, aromatic compounds can be rapidly decomposed without the possibility of the generation of carbon monoxide. In addition, gases having low decomposition voltages can be decomposed at a high decomposition rate.

Fourth Embodiment

Figure 9:
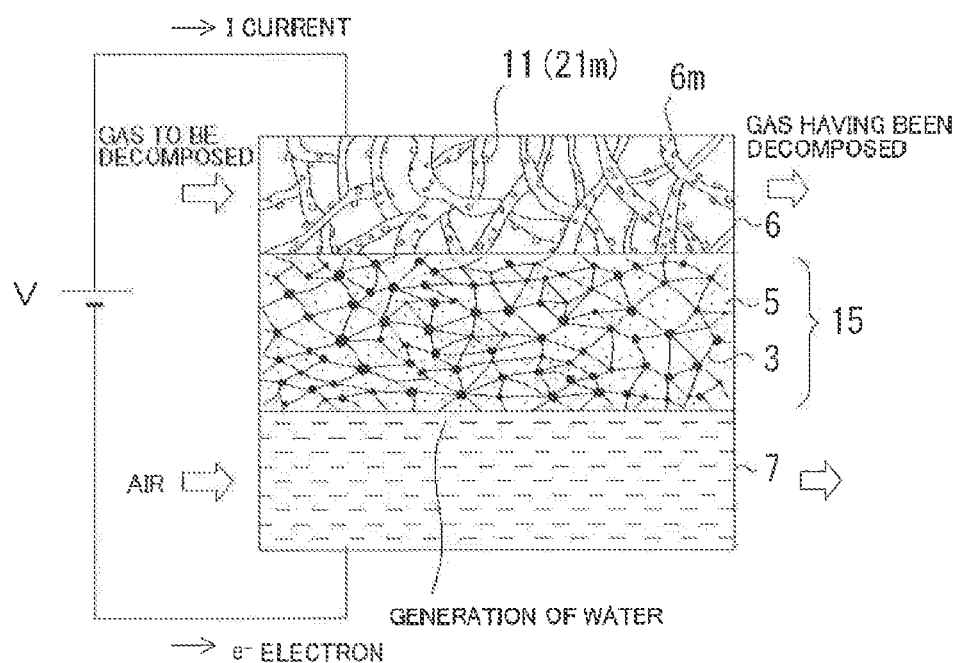
FIG. 9 is a sectional view illustrating a gas decomposition apparatus according to a fourth embodiment of the present invention.

FIG. 9 illustrates a gas decomposition apparatus 10 according to a fourth embodiment of the present invention. In this gas decomposition apparatus 10, the electrolyte layer 15 is constituted by Nafion, which is a PFC polymer 5 having a proton conductivity, and a biaxially stretched porous PTFE membrane 3 configured to mechanically reinforce the Nafion. The catalytic electrode layer 6 configured to decompose gases are constituted by a porous metal sheet 6m entirely formed by plating and fine catalytic particles 11 carried by the porous metal sheet 6m. It is not necessary to form the porous metal sheet 6m using a material other than the material of the gas-diffusion layer 8 in the first embodiment. The porous metal sheet 6m may be formed of the same material as that of the gas-diffusion layer 8. The fine catalytic particles 11 may be carried by other metal powder 21m. The counter electrode layer 7 is formed of porous carbon. Although the counter electrode layer 7 does not carry fine catalytic particles, the counter electrode layer 7 may carry fine catalytic particles. Since a reduction reaction occurs in the counter electrode layer (cathode) 7, even when a noncovalent carbon material is used for the counter electrode layer 7, there is no possibility that carbon monoxide is generated. Accordingly, due to a reason described below, porous carbon is preferably used.

As described above, the porous metal sheet 6m entirely formed by plating can be made to have a large pore size and a large porosity. Thus, the porous metal sheet 6m of the catalytic electrode layer 6 in FIG. 9 can make gas flow turbulent so that separation of gas from the surface layer is always repeated and new gas is supplied to the surface layer. Accordingly, an increase in the applied voltage is appropriately reflected to promote a decomposition reaction. As a result, while the applied voltage is increased, a decomposition reaction can be promoted without the possibility of the generation of carbon monoxide. In particular, in gas decomposition apparatuses used for deodorization of living spaces, the concentration of odorous gases is not high and hence the reaction tends to occur at a low frequency. In a laminar flow generated along a planar surface, there is a portion where the flow stagnates is generated in the surface layer. Such a stagnant portion is mainly constituted by non-reactive gases such as air. As a result, most odorous gas components at low concentrations pass without being brought into contact with the surface of the catalytic electrode layer 6. This is basically different from the case of fuel cells, which are configured to decompose large amounts of gas components at high concentrations. The porous metal sheet 6m entirely formed by plating is a three-dimensional network metal material having continuous pores. By decreasing the width of the frame portions of the metal material, the size of the pores can be increased. Furthermore, for example, the porosity and the relationship between specific surface and pore size can be controlled within wide ranges. Accordingly, by adjusting the pore size, the porosity, and the specific surface, a flow in which a portion in contact with the surface is always separated from the surface and new gas is made to be brought into contact with the surface can be formed. Thus, odorous gas components at low concentrations can be efficiently decomposed in a short period of time. Furthermore, the porosity can be made large and hence gases can be made to flow smoothly. As for the porous metal sheet 6m that is entirely formed by plating and can be made to have large values in terms of specific surface, porosity, and the like due to a large pore size and narrow frame portions, the above-described CELMET (registered trademark) is preferably used. CELMET is produced by steps sequentially performed as follows: a foaming treatment of a resin, a joining pore-formation treatment, electroless Ni plating, Ni electroplating, and removal of the resin. In the present embodiment, the porous metal material is entirely formed by plating. However, the porous metal material is not necessarily entirely formed by plating and may be partially formed by plating.

The catalytic particles 11 (21m) can be anchored (carried) on the porous metal sheet 6m by applying and drying a binder resin as in the first embodiment.

As illustrated in FIG. 9, the electrolyte layer 15 is constituted by the stretched porous PTFE membrane 3 and the PFC polymer 5 that fills gaps in the stretched porous PTFE membrane 3 and is in direct contact with the two electrodes 6 and 7. The PFC polymer 5 loses its ion conductivity unless it is wet. However, the PFC polymer 5 being wet has considerably low strength and is fragile. In particular, only repeating of drying and wetting of the PFC polymer 5 due to repeating of use and disuse can damage the PFC polymer 5. The stretched porous PTFE membrane 3 can reinforce the PFC polymer 5 to enhance the durability of the PFC polymer 5. In addition, the stretched porous PTFE membrane 3, which is porous, negligibly affects the ion conductivity.

The stretched porous PTFE 3 illustrated in FIG. 9 is not covered with a hydrophilic resin; however, the stretched porous PTFE 3 may be covered with a hydrophilic resin. By forming a hydrophilic resin film, a large number of micro-nodes and fibers running through the micro-nodes and the PFC polymer are further integrated, that is, the contact resistance between the PTFE and the PFC polymer is increased. Thus, the reinforcing effect provided by the PTFE is enhanced.

As for the stretched porous PTFE membrane 3, for example, POREFLON (registered trademark) manufactured by Sumitomo Electric Fine Polymer, Inc. is preferably used. In general, POREFLONs that are uniaxially and biaxially stretched (standard; biaxially stretched) and have a pore size of 0.2 to 1 μm (standard: 0.2 μm), a thickness of 10 to 25 μm (standard: 20 μm), and a porosity of 60% (standard: 70%) are preferably used. Among these POREFLONs, POREFLONs having a pore size of about 30 μnm (0.03 μm) can be made to have a fine pore size and a small thickness of 1 μm or less and further 0.1 μm or less. Thus, such POREFLONs are considerably advantageous for reducing the thickness of the electrolyte layer 15. By reducing the thickness of the electrolyte layer 15, the following significant advantages can be provided.

(1) Water generated in the counter electrode layer (cathode) 7 is readily distributed in the entirety of the PFC polymer 5. As described above, the PFC polymer 5 cannot exhibit proton conductivity without water. When the electrolyte layer 15 is thin, water generated at the interface between the counter electrode layer (cathode) 7 and the electrolyte layer 15 can readily moisten even the Interface between the catalytic electrode layer (anode) 6 and the electrolyte layer 15.

(2) The electrolyte accounts for a large portion of the internal resistance in the entire equivalent electric circuit. By reducing the thickness of the electrolyte, the current value can be increased, which is advantageous for promoting a decomposition reaction.

(3) A sufficiently high strength is also provided. The above-described POREFLON having a pore size of 30 nm has a thickness of 1 to 2 μm. When this POREFLON is used in the state of being bonded to a reinforcing film having a thickness of about 10 μm, in spite of the small thickness, sufficient reinforcement is achieved in terms of strength.

The gas decomposition apparatus 10 illustrated in FIG. 9 is intended to decompose odorous gases being mixed with air, such as ethanol, methanol, acetaldehyde, and formaldehyde. Thus, a potential is applied to the catalytic electrode layer (anode) 6 and the counter electrode layer (cathode) 7 such that odorous gases are decomposed by an oxidation reaction at the catalytic electrode layer 6. Specifically, protons are fed from the catalytic electrode layer 6 to the PFC polymer 5 of the electrolyte layer 15 to release electrons to external wiring. At this time, air containing odorous gases is introduced with a pump (not shown) into the catalytic electrode layer (anode) 6 and air (cleaned air) containing gases provided by decomposition through the anode reaction is discharged from the outlet to the ambient environment. At the counter electrode layer 7, protons having been conducted through the PFC polymer 5 of the electrolyte layer 15 cause a reduction reaction with air and electrons supplied from the wiring to the counter electrode layer (cathode) 7 to generate water. To supply air to the counter electrode layer 7, air is introduced to the counter electrode layer 7 from the outside. As described above, water generated at the counter electrode layer (cathode) 7 can moisten the PFC polymer 5.

To effectively distribute, in the electrolyte layer 15, water generated by the water generation reaction at the counter electrode layer 7, as described above, the electrolyte layer 15 preferably has a small thickness. In particular, in gas decomposition apparatuses used for deodorization of living spaces, the concentration of odorous gases is not high and hence the reaction tends to occur at a low frequency and the amount of water generated is small. Thus, reduction in the thickness of the electrolyte layer 15 or the PFC polymer 5 is an important factor. Furthermore, as described above, the electrolyte layer 15 is defined as electrical resistance in the gas decomposition apparatus 10. By reducing the thickness of the electrolyte layer 15, the electrical resistance is decreased. Accordingly, ion conductivity can be made high and the efficiency of gas decomposition can be enhanced.

The electrolyte layer 15 in the gas decomposition apparatus 10 according to the present embodiment can be produced by preparing and immersing the stretched porous PTFE membrane 3 so as to have a predetermined thickness in a solution having been obtained by dissolving a PFC polymer in a solvent, removing the solvent, and drying the membrane. At this time, to establish an electric contact between the catalytic electrode layer anode 6 and the counter electrode layer (cathode) 7, the PFC polymer 5 are made to be exposed on the front and back surfaces of the electrolyte layer 15. As described above, as for the catalytic electrode layer (anode) 6, metal powder 21*m* carrying the line catalytic particles 11 are preferably dispersed in and held by the porous metal sheet 6*m* while conductive contact is ensured. The counter electrode layer (cathode) 7 will be described below. The catalytic electrode layer (anode) 6 and the counter electrode layer (cathode) 7 are placed so as to sandwich the resultant electrolyte layer 15 from the front and back surfaces of the electrolyte layer 15. The catalytic electrode layer (anode) 6, the counter electrode layer (cathode) 7, and the electrolyte layer 15 are then heated at about 120° C. and bonded together by hot pressing to form, a membrane electrode assembly (MEA), which is a stack. Other than such a production method, various modified production methods may be employed: for example, a production method in which the electrolyte layer 15 is stacked on the electrodes layers 6 and 7.

As described above, in the counter electrode layer (cathode) 7, a reduction reaction occurs and carbon is not oxidized. Thus, a laminar porous material that is conductive and can hold conductive particles being dispersed therein is preferably used for the counter electrode layer (cathode) 7. For example, a porous sheet constituted by carbon fibers such as carbon paper or carbon felt is preferably used. In particular, a porous sheet constituted by carbon fibers has excellent resistance to strongly acidic atmosphere due to protons generated by a decomposition reaction. In addition, such a porous sheet is porous and hence can carry a large number of the fine catalytic particles 11 (metal powder 21*m*). Thus, the efficiency of decomposing odorous gases can be further enhanced, which is advantageous.

For example, the carbon paper may be produced by subjecting carbon fibers in the form of monofilaments to wet or dry paper making or the like so as to have any thickness or any basis weight. The carbon felt is produced by, for example, subjecting carbon fibers in the form of monofilaments to carding or the like, stacking on one another, and bonding together by a needle punching or the like. A carbon felt having any mean fiber size and any mass per unit area can be used. However, to reduce the thickness of a gas decomposition apparatus as much as possible, carbon paper is preferably used as a base.

As for the counter electrode layer (cathode) 7 in which fine catalytic particles are dispersed in and held by a conductive base such as carbon paper described above, cathodes having various structures may be employed. Specifically, as for the counter electrode layer (cathode) 7, (1) a structure in which fine catalytic particles are directly carried on the surfaces of a conductive base may be employed; or (2) composite particles in which the fine catalytic particles are carried on the surfaces of a conductive powder of carbon black or the like are dispersed in a binder resin having proton conductivity to provide a membrane and the membrane may be stacked on the surfaces of a conductive base. Such a catalytic electrode layer of (1) described above is prepared by, for example, in the state in which a conductive base is immersed in a solution containing metal ions serving as the source of fine catalytic particles, reducing the metal ions by the action of a reducing agent so that the metal ions are precipitated in the form of fine particles and directly carried on the surfaces of the conductive base (in the case of a porous conductive base, the surfaces include the inner surfaces of pores).

Fifth Embodiment

Figure 10:
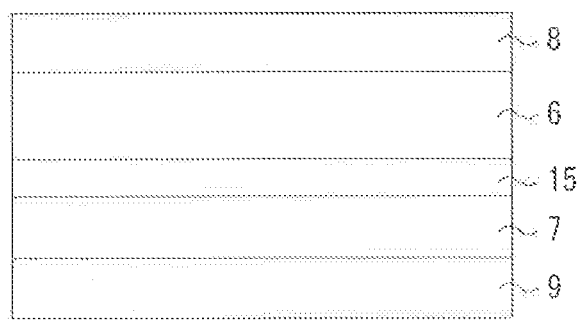
FIG. 10 is a schematic view of a stacked structure of a gas decomposition apparatus according to a fifth embodiment of the present invention.
Figure 11:
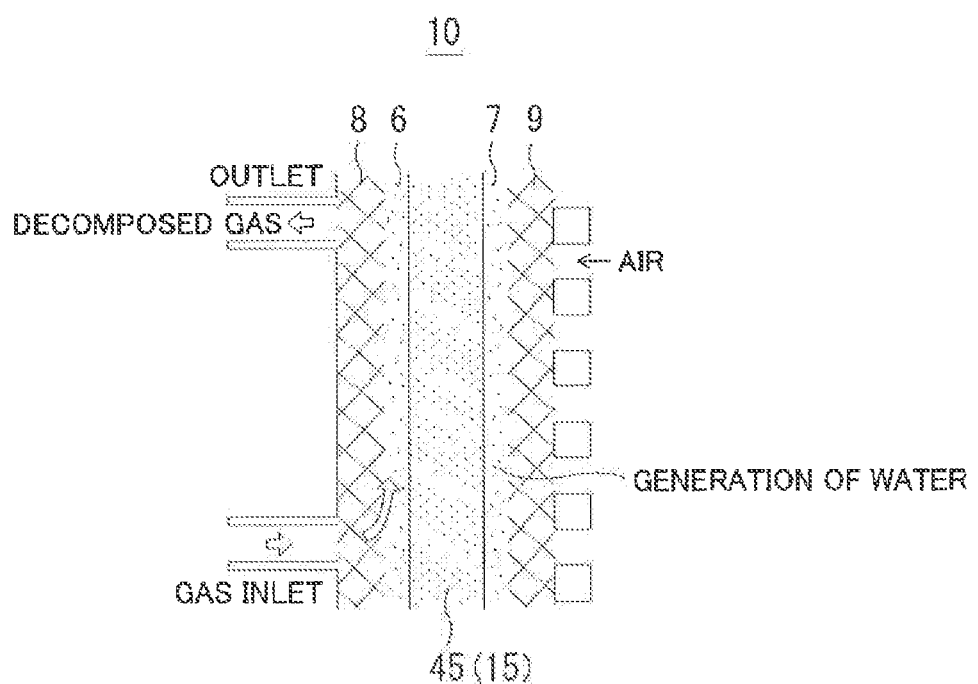
FIG. 11 is a sectional view illustrating a specific example of the gas decomposition apparatus illustrated in FIG. 10.

FIG. 10 is a schematic view of an MEA structure of a gas decomposition apparatus 10 according to a fifth embodiment of the present invention. FIG. 11 specifically illustrates the gas decomposition apparatus 10 having this MEA structure. In the MEA structure of the gas decomposition apparatus 10, a catalytic electrode layer 6 and a counter electrode layer 7 are disposed so as to sandwich an electrolyte layer (solid electrolyte) 15 that is a polymeric membrane containing an ionic liquid 45, the polymeric membrane being formed by dissolving and polymerizing vinyl monomers or the like serving as a resin material in an ionic liquid having high ion conductivity. Both the catalytic electrode layer 6 and the counter electrode layer 7 contain fine catalytic particles of platinum or the like. The fine catalytic particles may be contained in the two electrodes in the form of being carried by a conductive powder (carriers) or may be, without carriers, directly made to adhere to (be carried by) electrode sheets by plating or the like, the electrode sheets being conductive bases for forming the electrodes. A porous gas-diffusion layer 8 through which an odorous gas to be decomposed is introduced and from which the odorous gas having been subjected to a decomposition reaction (anode reaction or oxidation reaction) is discharged is provided for the catalytic electrode layer 6. The porous gas-diffusion layer 8 is preferably composed of a conductive material such as CELMET (registered trademark), which is a porous metal manufactured by Sumitomo Electric Industries, Ltd. A porous gas-diffusion layer 9 composed of CELMET or the like is also provided for the counter electrode layer 7 for the purpose of introducing air to provide oxygen for a cathode reaction and discharging water generated by the cathode reaction (reduction reaction).

The gas decomposition apparatus 10 has a feature that the electrolyte layer 15 is formed using the ionic liquid 45. Since ionic liquids have high ion conductivity, unlike existing gas decomposition apparatuses, stable molecules of toluene, benzene, and the like can be efficiently decomposed by applying a voltage equal to or higher than the decomposition voltage of water. The reason for this is as follows. Aromatic compounds such as toluene and benzene have higher decomposition voltages Vd than water. Ionic liquids are stable within and outside of the potential window corresponding to the decomposition voltages on the oxidation side and the reduction side. Accordingly, even when a voltage equal to or higher than Vd is applied between the anode and the cathode of the gas decomposition apparatus, toluene and benzene can be decomposed while a stable state is maintained. Ionic liquids are preferably in the form of solid thin membranes.

The application of ionic liquids to electrolytes of lithium cells, fuel cells, and the like has been studied. However, studies on the application of ionic liquids to gas decomposition apparatuses having MEA structures are unheard of. This is probably because, as described above (refer to FIG. 3), by using a PFC polymer (Nafion), even when a voltage higher than the decomposition voltage of water is applied between an anode and a cathode, the decomposition of odorous gases is seemingly performed without problems. When PFC polymers that have been proposed to date are used as electrolytes, odorous gases can be decomposed without problems under the application of a high voltage of about 2 V. However, use of PFC polymers as electrolytes, for example, in a long-term operation or a dry environment, probably causes the following problems. That is, the application of a voltage higher than the decomposition voltage of water results in a wasteful energy consumption with regard to the decomposition of water contained in PFC polymers; and a decrease in the gas decomposition rate due to use of electrical energy for the decomposition of water, the electrical energy being supposed to be used for the decomposition of gases.

The above-described problems cannot be found by simply producing or using gas decomposition apparatuses employing PFC polymers. This is because, as illustrated in FIG. 3, in use of PFC polymers for gas decomposition apparatuses, even when a voltage of about 2 V is applied between the anode and the cathode, seemingly normal gas decomposition appropriate to the applied voltage proceeds. However, the inventors of the present invention have studied the principle in which PFC polymers exhibit ion conductivity and the possibility of problems occurring in continuous use for a long period of time. As a result, the inventors have conceived the above-described application of ionic liquids to electrolytes. Hereinafter, components of the gas decomposition apparatus 10 in FIGS. 10 and 11 will be described.

(1) Electrolyte Layer 15

The ionic liquid 45 included in the electrolyte layer 15 is a salt also referred to as a low-temperature molten salt or a room-temperature molten salt. Ionic liquids are not clearly defined; however, ionic liquids generally refer to liquid salts that have substantially zero vapor pressure, are fire retardant and ionic, but have low viscosity and high decomposition voltage. Examples of typical ionic liquids are listed below in the form of being divided into cations and anions. However, another ionic liquid other than those listed below may be used.

Cation: one or more selected from trimethylpropylammonium (TMPA), trimethylmethoxymethylammonium (TM-MMA), trimethylphenylammonium (TMPhA), trimethylhexylammonium (TMHA), 1-ethyl-3-methylimidazolium (EMI), triethylsulfonium (TES), butylpyridinium (BP), 1-butyl-3-methylimidazole (BMI), and the like.

Anion: one or more selected from trifluoroxmethanesulfonylimide (TFSI), fluorosulfonylimide (FSI), trifluorosulfonylacetylimide (TSAC), trifluoromethanesulfonylmethyl (TFSM), trifluoromethanesulfate (TfO), $AlCl_4$ (chloroaluminate), $BF_4$ (tetrafluoroborate), $PF_6$ (hexafluorophosphate), F (fluoride), Cl (chloride), I (iodide), Br (bromide), and the like.

By using readily available ionic liquids in which the above-listed cations and anions are combined, electrolytes having low melting points, high decomposition voltages (stable in terms of voltage), and high ion conductivity can be obtained. For example, EMI+TFSI− is reduced at −2.1 V with respect to I+/I− (+1.1 V with respect to Li+/Li−) and is very stable. When EMI+TFSI− and TMHA+Tf2N− are measured in terms of cyclic voltammogram, the potential window extends from about −3.0 to +2.0 V, which is very large and stable compared with the potential window in terms of water. Accordingly, a gas decomposition apparatus employing an ionic liquid as an electrolyte can function with stability even when, for example, a voltage slightly exceeding 2.5 V, which is the decomposition voltage of toluene, is applied. Naturally, ethanol having a decomposition voltage of 1.3 V, acetaldehyde having a decomposition voltage of 1.2 V, and the like can be decomposed without problems.

(2) Gelatinization of Ionic Liquid

The electrolyte layer 15 in FIGS. 10 and 11 is a polymeric membrane containing an ionic liquid and has ion conductivity. Such a polymeric membrane containing an ionic liquid can be obtained by, for example, dissolving vinyl monomers in an ionic liquid and causing radical polymerization to proceed in the ionic liquid. At this time, the ionic liquid is contained in the network of the polymer and the state in which the ion conductivity of the ionic liquid is held in the network is obtained. This is a solid membrane obtained by gelatinizing the ionic liquid. Such a networked polymer may be synthesized by adding divinyl monomers to vinyl monomers. Such vinyl monomers and divinyl monomers are not limitative and any polymer may be employed as long as an ionic liquid is contained in a networked polymer by polymerization and the ion conductivity of the ionic liquid can be held in the polymer.

(3) Electrodes and Fine Catalytic Particles

As for a conductive base included in the catalytic electrode layer 6 or the counter electrode layer 7 containing a catalyst, a laminar base that has conductivity and can carry fine catalytic particles thereon can be used. For example, a porous sheet constituted by metal fiber obtained by processing nickel fine wires, niobium fine wires, or the like into a fibrous form; a porous metal material such as CELMET (a metal made porous by casting); a metal sinter; or carbon fiber such as carbon paper or carbon felt can be used. Since such a porous sheet is porous, fine catalytic particles can be directly carried on the porous sheet. Thus, it is not necessary to prepare carriers such as a powder. The term "powder" is a name that identifies the classification of a product. However, other than such a classification name for products, the term "powder" also refers to particles having a considerably larger size than fine catalytic particles.

As described below, such a porous sheet constituted by metal fiber, CELMET, or the like is preferred for preventing the generation of carbon monoxide when gas decomposition is performed at a temperature higher than room temperature by applying a voltage of 1.5 V or higher between the catalytic electrode and the counter electrode. However, when the temperature is not made higher than room temperature and a voltage of less than 1.5 V is applied between the two electrodes, there is no possibility that carbon monoxide is generated. In such cases, a porous sheet constituted by carbon fiber such as noncovalent carbon paper, carbon felt, or the like may be used. Such a porous sheet constituted by carbon fiber has excellent resistance to strongly acidic atmosphere containing protons generated by a gas decomposition reaction.

Figure 12:
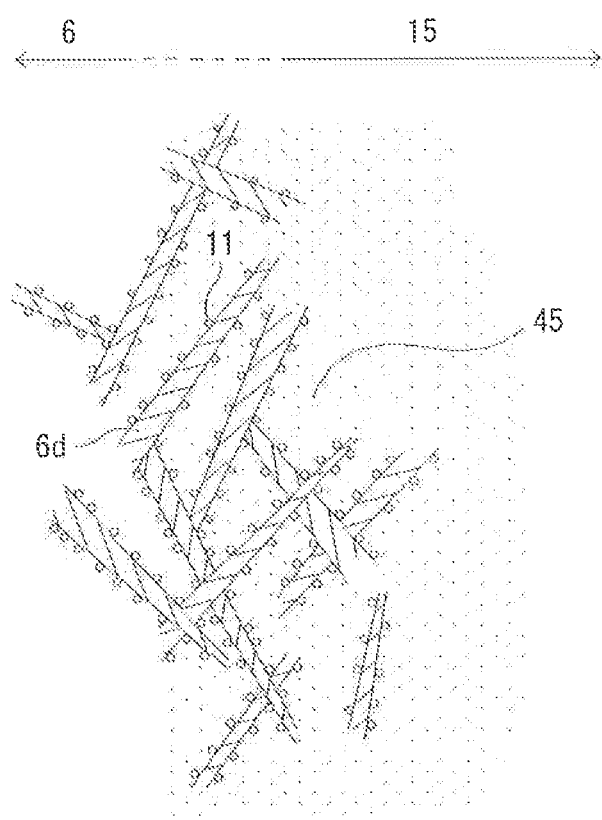
FIG. 12 is a sectional view illustrating a region near the interface between the catalytic electrode and the electrolyte of the gas decomposition apparatus illustrated in FIG. 10.

A conductive base containing fine catalytic particles may employ the following structures. (1) As illustrated in FIG. 12, fine catalytic particles 11 are directly carried by the surface of the above-described porous conductive base 6$d$. The conductive base 6$d$ may be metal fiber, CELMET, or the like, or carbon fiber.

Figure 13:
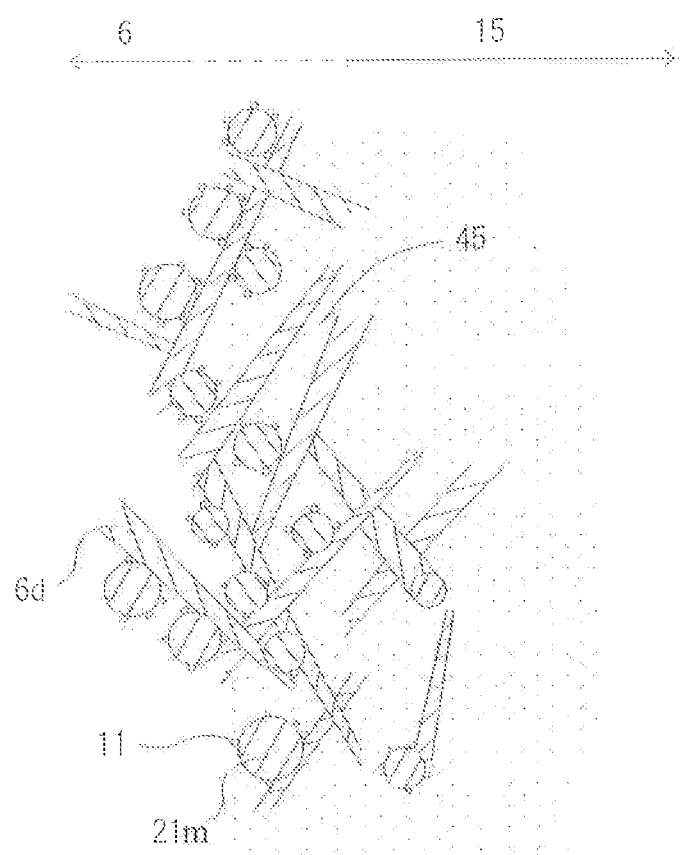
FIG. 13 is a sectional view illustrating a region near the interface between the catalytic electrode and the electrolyte of a gas decomposition apparatus other than the gas decomposition apparatus illustrated in FIG. 10.

(2) As illustrated in FIG. 13, the structure in which a metal powder (carriers) 21$m$ of nickel, cobalt, silver, molybdenum, or the like on the surfaces of which the fine catalytic particles 11 are carried are dispersed in a binder resin having proton permeability and provided on the surface of the conductive base 6$d$ can be employed. As for the powder, other than the above-described metal powder, a conductive carbon powder 21$d$ of carbon black, acetylene black, or the like may be used. The conductive carbon powder 21$d$ may be used as carriers; and the carriers may be made to carry the fine catalytic particles 11, and dispersed in the binder resin, and provided on the surface of the conductive base 6$d$, As for the catalytic electrode layer 6 in (1) above (although "the counter electrode layer 7 containing a catalyst" is also included, the description thereof is omitted for the sake of simplicity), for example, in the state in which the conductive base 6$d$ is immersed in a solution containing metal ions forming the fine catalytic particles 11, the metal ions are reduced with a reducing agent to precipitate the fine catalytic particles 11 composed of the metal onto the conductive base 6$d$. As described above, when a porous sheet is used as the conductive base, the fine catalytic particles also precipitate onto the inner surfaces of many pores. In such precipitation, the fine catalytic particles are carried by the conductive base.

A catalytic electrode layer in (2) above is formed as follows. For example, a metal powder 21$m$ of nickel, silver, or the like or a conductive carbon powder 21$d$ of carbon black or the like is prepared. In the same manner as described above, such a powder 21$m$, 21$d$ is then immersed in a solution containing metal ions forming fine catalytic particles and the metal is precipitated in the form of fine particles onto the surfaces of the conductive powder by using a reducing agent. The catalyst-carrying powder 21$m$, 21$d$, 11 is mixed with a solution of a binder resin having ion permeability to prepare a coating solution. The coating solution is then applied to a surface of the conductive base and dried to form a binder resin membrane in which the carrier powder is dispersed. In the catalytic electrode layer of (2) above, as described above, porous metal fiber such as nickel fiber or niobium fiber; a porous metal material such as CELMET; a metal sinter; carbon fiber such as carbon paper; or the like is used as the conductive base. In addition, the binder resin membrane is stacked so as to be in contact with the electrolyte.

In such a stack, while the contact between the fine catalytic particles and odorous components Is maintained with the porous conductive base, the catalyst-carrying powder is dispersed in a membrane composed of a binder resin having proton permeability, and the membrane is sandwiched between the conductive base and the solid electrolyte. Accordingly, for example, removal of the fine catalytic particles is suppressed and hence the catalytic action can be maintained for a longer period of time.

As for the fine catalytic particles, a rare metal such as platinum, ruthenium, palladium, iridium, or osmium; an iron group metal such as iron, cobalt, or nickel; or a noble metal such as vanadium, manganese, silver, or gold is preferably used. Alternatively, to enhance a special function, fine catalytic particles composed of an alloy of such metals may be used. For example, to enhance a catalyst-poison resistance serving as a catalytic function, an alloy in which the mass ratio of platinum to palladium Pt/Pd satisfies about 7/3 to 9/1 may be used.

In the gas decomposition apparatus 10, by applying a voltage of, for example, about 1.5 V to the two electrodes at room temperature, odorous gases such as acetaldehyde, ethanol, and toluene can be rapidly decomposed at a high, energy efficiency. For example, when the electrolyte includes a PFC polymer such as Nafion, the application of a voltage of 1.5 V between the two electrodes causes the electrolysis of water. Thus, supplied energy is used for the electrolysis of water and hence the energy efficiency is degraded. In addition, since the water in Nafion is decomposed, moisture necessarily required for ion conduction is decreased to less than the appropriate amount. Thus, the ion conductivity is degraded and the possibility of the termination of gas decomposition is caused. As in a gas decomposition apparatus according to the present embodiment, by using an ionic liquid for an electrolyte, a stable state can be maintained under the application of voltage. In addition, by using a polymeric membrane containing an ionic liquid, since the ionic liquid can be handled as a solid electrolyte membrane, the production of such a gas decomposition apparatus can be simplified.

Sixth Embodiment

The structure of a gas decomposition apparatus according to a sixth embodiment of the present invention is the same as that illustrated in FIGS. 10 and 11. Use of the ionic liquid 45 for the electrolyte layer 15 is also the same. The feature of the gas decomposition apparatus 10 of the present embodiment is that, to prevent the possibility of the generation of carbon monoxide even when a voltage of higher than 1.5 V is applied between the catalytic electrode layer 6 and the counter electrode layer 7, noncovalent carbon materials are not disposed as conductive materials in contact with the fine catalytic particles 11. The gas decomposition apparatus 10 according to the fifth embodiment is the same as in the present embodiment as long as a metal is used for the conductive base of the catalytic electrode layer 6 or a metal is used for the catalyst carrier powder. However, the present embodiment is different from the fifth embodiment in that, to provide a configuration in which the possibility of the generation of carbon monoxide is prevented with certainty, configurations in which fine catalytic particles are directly carried by noncovalent carbon fiber or the like are excluded.

FIG. 2 described above is a graph illustrating experimental results serving as the reason why a gas decomposition apparatus according to the present embodiment is provided. FIG. 2 illustrates experimental results of a gas decomposition apparatus in which platinum was used for fine catalytic particles, carbon black was used for catalyst carriers, carbon paper was used for the conductive base of a catalytic electrode, and Nafion (PFC polymer) was used for an electrolyte. Both the carbon black of the catalyst carriers and the carbon paper of the conductive base are noncovalent. FIG. 2 shows that the application of a voltage of 1.5 V between the two electrodes at 80° C. results in the generation of carbon monoxide. In addition, the application of a voltage of 2 V at room temperature also results in the generation of carbon monoxide. Sources of the generation of carbon monoxide other than the air are the above-described carbon materials. Decomposition of gases that are not limited to hydrocarbons occurs at a position where the fine catalytic particles 11, the catalytic electrode layer 6 (catalyst carriers 21 in the case of using catalyst carriers), and the electrolyte layer 15 are in contact with each other. Carbon monoxide is generated when noncovalent carbon black or noncovalent carbon paper is present in such a contact position.

FIG. 3 described above, which is not directly related to the generation of carbon monoxide, is a graph illustrating the influence of the voltage between the anode and the cathode on the decomposition rate of acetaldehyde decomposed with the gas decomposition apparatus described in conjunction with FIG. 2. FIG. 3 indicates that, as the voltage between the two electrodes increases from 1 V to 1.5 V to 2 V, the concentration of acetaldehyde decreases in a shorter time. As described above, this gas decomposition, apparatus contained Nafion; however, the gas decomposition process was seemingly performed without problems under the application of a voltage of 2 V. In spite of such a gas decomposition process, the inventor of the present invention has concluded that, when an aromatic compound gas is decomposed, use of an ionic liquid for an electrolyte is advantageous in continuous use for a long period of time or in dry environments.

(Catalytic Electrode and Fine Catalytic Particles in the Present Embodiment)

Figure 14:
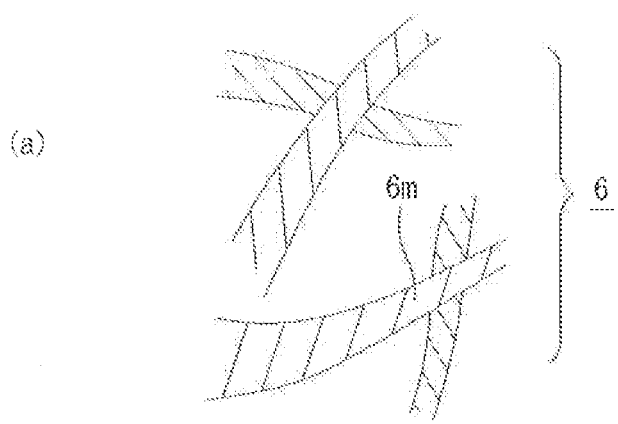
FIG. 14 illustrates conductive bases of the catalytic electrode of a gas decomposition apparatus according to a sixth embodiment of the present invention; (a) illustrates a conductive base of metal fiber or the like; and (b) illustrates carbon fiber, metal fiber, or the like that has been covered with a conductive-diamond thin film.
Figure 14:
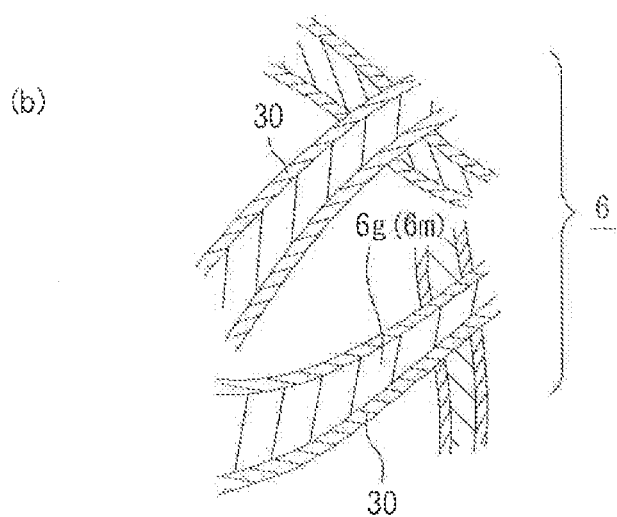

As for a conductive base included in the catalytic electrode layer, a laminar base that has conductivity and can carry fine catalytic particles thereon can be used. For example, as illustrated in FIG. 14(a), a porous sheet constituted by metal fibers such as nickel fine wires or niobium fine wires or a porous metal material sheet 6m such as CELMET is preferred. Such a porous sheet constituted by metal fibers, the porous metal material sheet 6m, or the like is preferred in view of prevention of the generation of carbon monoxide caused by the above-described mechanism.

As illustrated in FIG. 14(b), in spite of employing noncovalent conductive base 6g of carbon fiber as frames, a conductive base including a surface layer of the conductive diamond 30 containing an impurity such as boron at a high concentration can be used without problems. In the conductive diamond 30, since carbon atoms are bonded through covalent bonds, the conductive diamond 30 not only has high strength but also has high resistance to external voltage and is very stable against external voltage compared with noncovalent carbon black, graphite, and the like. The frames on which a thin film of the conductive diamond 30 is formed may be, for example, the above-described porous metal sheet 6m or the porous conductive base 6g of carbon fiber such as carbon paper or carbon felt. Even after a thin film of the conductive diamond 30 is formed on the porous frames, the resultant material is desirably still porous. In the above-described cases, the fine catalytic particles are made not to be in direct contact with noncovalent carbon materials such as carbon paper and carbon felt.

A conductive base including fine catalytic particles may employ the following structures. (1) The line catalytic particles are directly carried on a surface of the conductive base. The surface of the conductive base may be a layer formed of conductive diamond or may be metal fiber or the like of the conductive base.

Figure 15:
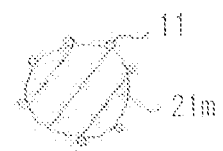
FIG. 15 illustrates catalyst-carrying powders in a gas decomposition apparatus according to the sixth embodiment of the present invention; (a) illustrates a metal powder having been made to carry fine catalytic particles; and (b) illustrates a noncovalent carbon powder, metal powder, or insulating powder having been subjected to a conductive-diamond coating treatment and then having been made to carry fine catalytic particles.
Figure 15:
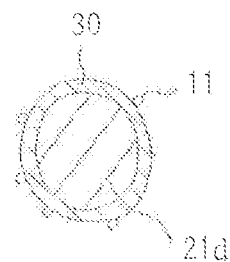

(2) As illustrated in FIG. 15(a), a structure in which a metal powder (carriers or nugget-shaped carriers) 21m of nickel, cobalt, silver, molybdenum, or the like on the surface of which the fine catalytic-particles 11 are carried are dispersed in a binder resin, having proton permeability and provided on a surface of the conductive base can be employed. Alternatively, as illustrated in FIG. 15(b), other than the above-described metal powder, a conductive carbon powder 21d of carbon black, acetylene black, or the like may be used. In this case, the thin film(s) of the conductive diamond 30 must be formed on the surfaces of the conductive carbon powder 21d. Such (conductive carbon powder 21/surface layer of the conductive diamond 30) may be used as carriers; and the carriers may be made to carry fine catalytic particles, dispersed in the binder resin, and provided on the surface of the conductive base. Core parts of the earners such, as conductive carbon powder 21d or the like in FIG. 15(b) may be an insulating powder and the electrical connection between the carriers and the catalytic electrode layer 6 can be established through films of the conductive diamond 30.

As for the catalytic electrode layer 6 in (1) above, for example, in the state in which the conductive base is immersed in a solution containing metal ions forming the fine catalytic particles the metal ions are reduced with a reducing agent to precipitate the fine catalytic particles composed of the metal onto the conductive base. As described above, when a porous sheet is used as the conductive base, the fine catalytic particles also precipitate onto the inner surfaces of many pores. In such precipitation, the fine catalytic particles are carried by the conductive base.

A catalytic electrode layer in (2) above is formed as follows. For example, (i) a metal powder of nickel, silver, or the like, (ii) a powder in which conductive-diamond, surface layers are formed on a metal powder, (iii) a composite carbon powder in which conductive-diamond thin films are formed on the surfaces of a conductive carbon powder such as carbon black, or (iv) a powder in which conductive-diamond thin films are formed on an insulating powder is prepared. In the same manner as described above, such a conductive powder is then immersed in a solution containing metal ions forming fine catalytic particles and the metal is precipitated in the form of fine particles onto the surfaces of the conductive powder by using a reducing agent. The catalyst-carrying powder is mixed with a solution of a binder resin having ion permeability to prepare a coating solution. The coating solution is then applied to the surface of the conductive base and dried to form a binder resin membrane in which the carrier powder is dispersed. In the catalytic electrode layer of (2) above, as described above, porous metal fiber or the like such as nickel fiber or niobium fiber, a porous material obtained by coating such metal fiber or the like with conductive diamond, a porous material obtained by coating carbon fiber such as carbon paper with a conductive-diamond thin film, or the like is used as the conductive base. In addition, the membrane of the binder resin is stacked so as to be in contact with the electrolyte.

In such a stack, while the contact between the fine catalytic particles and odorous components is maintained with the porous conductive base, the catalyst-carrying powder is dispersed in a membrane composed of a binder resin having proton permeability, and the membrane is sandwiched between the conductive base and the solid electrolyte. Accordingly, for example, removal of the fine catalytic particles is suppressed and hence the catalytic action can be maintained for a longer period of time.

In a gas decomposition apparatus according to the present embodiment, the electrolyte is formed using an ionic liquid. Thus, gas decomposition can be performed while a voltage equal to or higher than the decomposition voltage of water is applied to the two electrodes. At this time, the possibility of the generation of carbon monoxide can be prevented. Therefore, odorous gases of many types including toluene, ethanol, and the like can be rapidly decomposed with a high energy efficiency while safety is ensured.

Instead of an ionic liquid, in the fifth and sixth embodiments, $CsHSO_4$, a molten salt, or a solid oxide electrolyte functioning under heating may be used. Thus, the scope of selection of the electrolyte can be expanded in accordance with, for example, the operation environment, required performance, or required cost effectiveness of the gas decomposition apparatus. For example, since $CsHSO_4$ can function at a low temperature of about 10° C., $CsHSO_4$ is suitable for applications in which cost effectiveness and high decomposition capability are required. Ionic liquids are suitable for applications in which small size, low power, and the like are of higher priority than cost effectiveness. Solid oxide electrolytes, which need to be heated to high temperature of 300° C. or higher, are suitable for applications in which high decomposition capability, durability, being field-proven, cost effectiveness, and the like are of high, priority.

Seventh Embodiment

Figure 16:
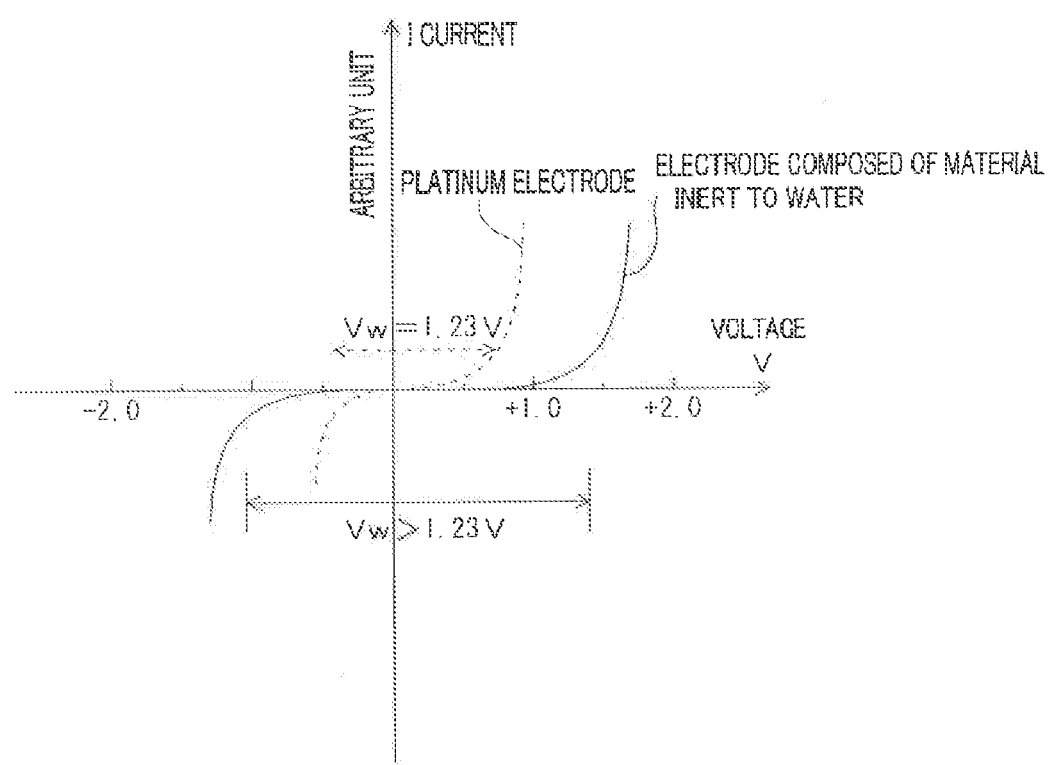
FIG. 16 is a schematic graph, illustrating voltage-current curves obtained when an electrode of an existing gas decomposition apparatus is immersed in water and an electrode of a gas decomposition apparatus according to the present invention is immersed in water.

The configuration of a gas decomposition apparatus according to a seventh embodiment of the present invention is the same as that of the gas decomposition apparatus 10 illustrated in FIG. 1. However, the present embodiment is unique with regard to the material of a portion of an electrode, the portion being in contact with the electrolyte. The present invention has a feature that a portion of a decomposition-side electrode layer 6, the portion being in contact with the electrolyte, is composed of a material that is inert to water. FIG. 16 illustrates voltage-current curves obtained when a standard hydrogen electrode (SHE) is defined as zero potential, an electrode being immersed in water is used as a working electrode, and potential is applied to the working electrode. When a platinum electrode is used as the working electrode (a broken line in FIG. 16), in the positive region, the current density exponentially increases beyond about +0.5 V; and in the negative region, the current density exponentially increases in the opposite direction beyond −0.3 V toward negative potential. Current substantially does not flow between the current rising potential in the positive region and the current rising potential in the negative region. Such a potential range or a potential width Vw where current substantially does not flow is referred to as a window. For water, Vw is 1.23 V. The potential width Vw of the window depends on the material (water in the present case) into which the electrode is immersed. As for the material of the electrode, the potential width Vw of the window does not vary as long as electrodes composed of the platinum group and the like having high catalytic activity are used. In the positive region, as the current increases, oxygen is generated at the working electrode; and in the negative region, as the current increases, hydrogen is generated.

In the above-described measurement of potential with water or an aqueous solution, the reference electrode is preferably a silver/silver chloride electrode (Ag/AgCl electrode), mercury/mercurous chloride electrode (calomel electrode, $Hg/Hg_2Cl_2$ electrode), a hydrogen, electrode, or the like. As for the working electrode (work electrode), an appropriate electrode material considerably varies; however, in the case of water, platinum (Pt), carbon (C), mercury (Hg), or the like is preferably used. Flow of current needs to be suppressed as much as possible. Accordingly, potentiometry in which measurement is performed in the state where current does not flow through the system is preferably used. Alternatively, it is preferred that an auxiliary electrode for undertaking current other than the reference electrode be prepared and a three-electrode potentiostat be used. In addition, since there are many variable factors (disturbance factors) in the measurement of potential, extreme caution must be taken.

However, when a material that does not have a high catalytic activity, for example, a material that is inert to water is used for the working electrode, the current rising potential in the positive region becomes high compared with a catalytic electrode having high catalytic activity and the current rising potential in the negative region shifts toward the negative direction. Thus, in spite of use of the same water, the window extends. For example, a working electrode covered with conductive diamond has a window having a potential width of about 2.5 V. That is, when the working electrode is formed of a material that is inert to water, water is not decomposed and a stable state is maintained even under the application of a higher voltage. Accordingly, when a material that is inert to water is used for the decomposition-side electrode, even when an electrolyte containing water is used, odorous gases can be decomposed under the application of a voltage of 1.23 V or higher between the decomposition-side electrode and the counter electrode without decomposing the water in the electrolyte. As for the decomposition-side electrode, a wide window is preferred in view of maintaining water in a stable state. However, a further shift of the current rising potential in the negative region toward the negative direction is more preferred in view of decomposing odorous components and generating protons without decomposing water at the decomposition-side electrode. According to the present invention, a material that is inert to water is used for a portion of the decomposition-side electrode 6, the portion being in contact with the electrolyte. Thus, even when the electrolyte contains water, odorous gas components can be decomposed without decomposing the water in the electrolyte.

Figure 17:
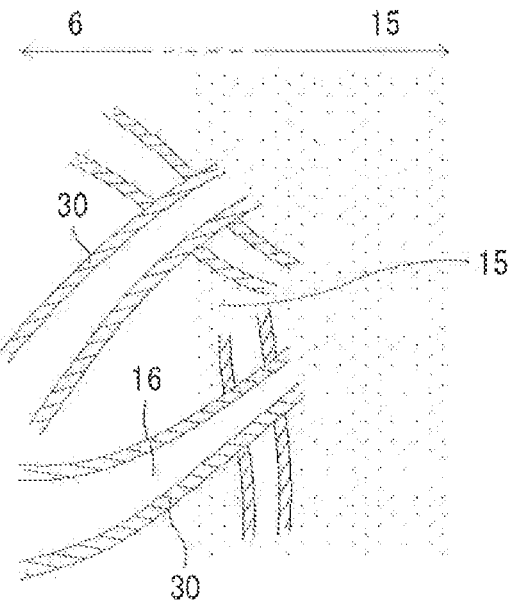
FIG. 17 illustrates an electrolyte-side portion of the decomposition-side electrode of a gas decomposition apparatus according to a seventh embodiment of the present invention.

FIG. 17 illustrates an electrolyte-side portion of the decomposition-side electrode layer 6 of a gas decomposition apparatus according to the seventh embodiment of the present invention. The present embodiment has a feature that the decomposition-side electrode layer 6 is prepared with a porous sheet 16 covered with a thin film of the conductive diamond 30. The core material of the porous sheet 16 of the decomposition-side electrode layer 6 may be any material such as a metal, an insulating material, a noncovalent carbon fiber, or the like; preferably, Si, Mo, Nb, a metal oxide ceramic, or the like. The conductive diamond, which is crystals in which carbon atoms are covalently bonded together, has been made to have conductivity by being doped with an impurity such as boron at a high concentration. The conductive diamond is not restricted to covalently bonded carbon crystals and may be a material referred to as a diamond like material as long as it contains an impurity element at a high concentration and has electrical conductivity.

When the porous sheet 16 is formed of a metal, any porous metal such as metal fiber obtained by processing nickel fine wires, niobium fine wires, or the like into a fibrous form; a porous metal material such as CELMET (a metal made porous by casting); or a metal sinter obtained by sintering a metal powder may be used. The electrolyte layer 15 may be a PFC polymer, any aqueous electrolyte, or any nonaqueous electrolyte. As for such a nonaqueous electrolyte, for example, an ionic liquid may be used. Fine catalytic particles are not used.

When the porous sheet covered with the thin film(s) of the conductive diamond 30 is a fibrous sheet, it is preferred that the thin film(s) of the conductive diamond 30 be formed on threads and the threads be then woven together. In the case of a porous metal material such as CELMET, it is preferred that the porous metal material be placed in a plasma CVD chamber, irradiated with carbon plasma, and doped with a p-type impurity such as boron at a high concentration to form the thin film(s) of the conductive diamond 30 both on an outer surface and an inner surface of the porous material. A porous insulating material can be treated in the same manner.

Eighth Embodiment

Figure 18:
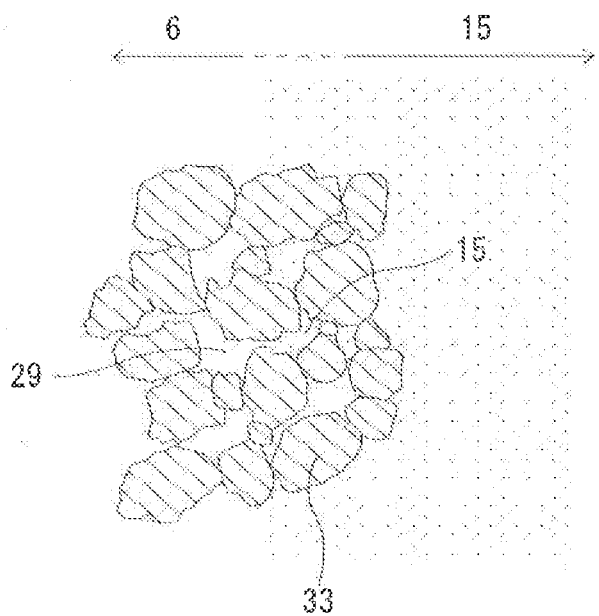
FIG. 18 illustrates an electrolyte-side portion of the decomposition-side electrode of a gas decomposition apparatus according to an eighth embodiment of the present invention.

FIG. 18 illustrates an electrolyte-side portion of a decomposition-side electrode layer 6 of a gas decomposition apparatus according to an eighth embodiment of the present invention. The present embodiment has a feature that an inert powder 33 that is inert to water such as $Ti_4O_7$ powder or $PbO_2$ powder is used for a porous conductive base. In FIG. 18, the porous decomposition-side electrode layer 6 is formed by sintering the inert powder 33. In the inert powder 33, there are gaps or pores 29. As long as the decomposition-side electrode layer 6 is porous and has conductivity, the decomposition-side electrode layer 6 is not necessarily formed from a single powder.

The $Ti_4O_7$ powder and the $PbO_2$ powder are well-known powder materials and commercially available products thereof may be used. As for the technique of forming the decomposition-side electrode layer 6 from $Ti_4O_7$ powder or $PbO_2$ powder, a well-known powder sintering technique can be used. The porosity in terms of many pores can be adjusted with pressure applied, upon pressing $Ti_4O_7$ powder or $PbO_2$ powder charged in a mold for the decomposition-side electrode layer 6 and the particle size (particle diameter) of such a powder.

As for the inert powder 33, for example, $Ti_4O_7$ is one of compounds referred to as Magneli phases and exhibits metallic conductivity at room temperature due to contribution of delocalized $3d$ electrons of titanium to electrical conductivity. $PbO_2$ is a conductive material having been used for positive plates of lead-acid batteries. Such $Ti_4O_7$ and $PbO_2$ are inert to water, expand the window in terms of water illustrated in FIG. 16, and shift further the current rising potential in the negative region toward the negative direction.

Accordingly, in the state in which a voltage of the decomposition voltage of water (1.23 V) or higher is applied between the decomposition-side electrode and the counter electrode, water is not decomposed. Thus, by applying such a high voltage, the decomposition rate of odorous components can be increased and odorous gases having high decomposition voltages such as aromatic compounds can be decomposed with a high energy efficiency. As a result, while a PFC polymer electrolyte that necessarily requires water such as Nafion or an aqueous electrolyte is used, lasting stability for the state in which the above-described preferred advantages are exhibited under the application of a voltage equal to or higher than the decomposition voltage of water can be achieved.

The electrolyte is not restricted to PFC polymers and may be an electrolyte that does not require or contain water. For example, the electrolyte may be (1) a room-temperature molten salt or an ionic liquid functioning at room temperature or (2) $CsHSO_4$, a phosphoric acid-based proton conductor such as $(NH_4)_2K_{1-x}PO_3$, a molten salt, or a solid oxide electrolyte functioning under heating. Alternatively, phosphoric acid may be used as the electrolyte. Thus, the scope of selection of the electrolyte can be expanded in accordance with, for example, the operation environment, required performance, or required cost effectiveness of the gas decomposition apparatus. For example, since $CsHSO_4$ can function at a low temperature of about 100° C., $CsHSO_4$ is suitable for applications in which cost effectiveness and high decomposition capability are required. Ionic liquids are suitable for applications in which small size, low power, and the like are of higher priority than cost effectiveness. Solid oxide electrolytes, which need to be heated to a high temperature of 300° C. or higher, are suitable for applications in which high decomposition capability, durability, being field-proven, cost effectiveness, and the like are of high priority.

Ninth Embodiment

Figure 19:
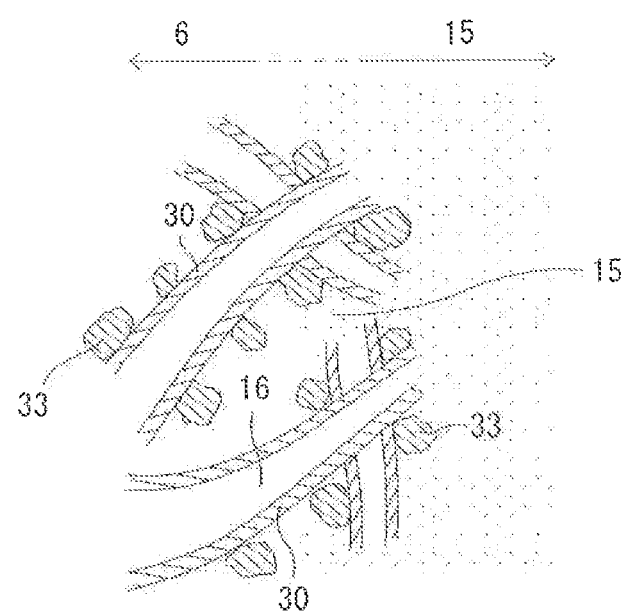
FIG. 19 illustrates an electrolyte-side portion of the decomposition-side electrode of a gas decomposition apparatus according to a ninth embodiment of the present invention.

FIG. 19 illustrates an electrolyte-side portion of a decomposition-side electrode layer 6 of a gas decomposition apparatus according to a ninth embodiment of the present invention. The present embodiment has a feature that a porous sheet covered with conductive diamond 30 illustrated in FIG. 17 is used and an Inert powder 33 that is inert to water such as $Ti_4O_7$ powder or $PbO_2$ is made to adhere to the porous sheet. When the decomposition-side electrode layer 6 has the structure illustrated in FIG. 17, the surface area of regions where odorous gases can be decomposed is increased and projected portions (inert powder 33 itself) that are highly frequently in contact with odorous gases can be formed.

The decomposition-side electrode layer 6 is preferably produced by dispersing the inert powder 33 in a binder resin having ion permeability and placing the inert powder 33 on a porous sheet covered with the conductive diamond 30. In this case, the inert powder 33 is mixed with a solution of the binder resin having ion permeability to prepare a coating solution. The coating solution is then applied to a surface of the porous sheet covered with the conductive diamond and dried. Thus, a binder resin membrane in which the inert powder 33 is dispersed is formed. As for the porous sheet to be covered with conductive diamond, as described above, porous metal fiber such as nickel fiber or niobium fiber; a porous metal material such as CELMET: a metal sinter; carbon fiber such as carbon paper; insulating fiber; or the like may be used. The binder resin membrane is stacked so as to be in contact with the electrolyte.

In the above-described configuration of the decomposition-side electrode layer 6, when a voltage equal to or higher than the decomposition voltage of water is applied between the decomposition-side electrode layer 6 and the counter electrode layer 7, since the inert powder 33 projects from the surface of the base, the decomposition of odorous gases can be promoted on the surface of the inert powder 33 by (1) an increase in the surface area, (2) an increase in the frequency of the contact with odorous gases, and (3) other unknown reasons. As a result, while a perfluorocarbon polymer electrolyte that necessarily requires water such as Nafion or an aqueous electrolyte is used, lasting stability for the state in which odorous components of many types can be decomposed at a high rate under the application of a voltage equal to or higher than the decomposition voltage of water can be achieved.

(Regarding Application of Voltage and Potential)

As illustrated in FIG. 9, the application of the voltage V of the voltage source to the gas decomposition apparatus 10 does not result in the application of the voltage V itself between the catalytic electrode layer anode 6 and the counter electrode layer (cathode) 7. This has been repeatedly described. When the (catalytic electrode layer anode 6/electrolyte layer 15/the counter electrode layer (cathode) 7) is seen as a single gas decomposition apparatus 10, the gas decomposition apparatus 10 includes an internal resistance $R_{in}$. Accordingly, when the gas decomposition apparatus 10 is being operated and current I is passed through the gas decomposition apparatus 10, a voltage drop of $R_{in} \times I$ occurs at the internal resistance $R_{in}$. In general, since there are a plurality of points contributing to the internal resistance, a voltage drop occurs at each point and the total of the voltage drops is $R_{in} \times I$. As a result, voltage $V_{ef}$ that is effectively applied to the gas decomposition apparatus 10 is $V_{ef} = V - R_{in} \times I$. The internal resistance $R_{in}$ considerably varies in accordance with the material of the electrolyte, the thickness of the electrolyte, the state in which the catalytic electrode layer (anode) 6, the counter electrode layer (cathode) 7, and the electrolyte layer 15 are in contact with each other, and the like. Even in electrochemical systems of a single type, the internal resistance $R_{in}$ can vary in accordance with production chance and from lot to lot.

By measuring potentials at points in the (catalytic electrode layer (anode) 6/electrolyte layer 15/the counter electrode layer (cathode) 7), that is, by determining the distribution of potentials, the degree of contribution of each component to the internal resistance can be determined. In addition, the voltage $V_{ef}$ that effectively contributes to the electrochemical reaction of the gas decomposition apparatus 10 can also be determined. In the measurement of potential, a potentiostat including a reference electrode of platinum (Pt), silver (Ag), or the like is used. Furthermore, it is necessary to adjust influencing factors such as temperature to standard conditions. Only in this case, meaningful results that are comparable with other measurement data (potential values) were obtained. Accordingly, "the voltage applied to the gas decomposition apparatus 10" and the like should not be compared with other similar data without thought. In contrast, the source voltage V is at least practically clear. In addition, a voltage source having a predetermined performance (nominal voltage) is provided assuming that the voltage source enables actual operation of the gas decomposition apparatus 10 as long as the internal resistance does not excessively change. Accordingly, the output voltage or the nominal voltage of a voltage source is an indicator that is practically less likely to cause problems in comparison with others.

Embodiments of the present invention have been described. However, the embodiments disclosed above are mere examples of the present invention and the scope of the present invention is not restricted to these embodiments. The scope of the present invention is defined by the descriptions of Claims and the present invention encompasses all the modifications falling within the meaning and scope equivalent to the descriptions of Claims.

INDUSTRIAL APPLICABILITY

According to a gas decomposition apparatus and a gas decomposition method according to the present invention, gases having high decomposition voltages such as aromatic compounds can be rapidly decomposed without the possibility of the generation of carbon monoxide and gases having low decomposition voltages can be decomposed at a high decomposition rate. Therefore, the present invention is expected to contribute to rapid decomposition of odors in places crowded with people, indoors, and the like.

REFERENCE SIGNS LIST 3 stretched porous PTFE membrane
5 PFC polymer
6 catalytic electrode layer (decomposition-side electrode layer)
6d conductive base of catalytic electrode layer
6g conductive base of carbon fiber
6m porous metal sheet (conductive base of metal fiber or the like)
7 counter electrode layer (catalytic electrode layer)
8, 9 gas-diffusion layer
10 gas decomposition apparatus
11 fine catalytic particles
15 electrolyte layer
16 porous sheet
21 carrier (powder)
21m metal powder
21d conductive carbon powder
29 pore
30 conductive diamond
33 powder inert to water ($Ti_4O_7$ powder or $PbO_2$ powder)
45 ionic liquid

The invention claimed is:

1. A gas decomposition apparatus comprising:
a decomposition-side electrode being a porous electrode having a gas inlet into which gas containing a component to be decomposed is introduced;
a counter electrode that forms a pair with the decomposition-side electrode and is porous; and
an electrolyte sandwiched between the decomposition-side electrode and the counter electrode,
wherein a portion of the decomposition-side electrode, the portion being in contact with the electrolyte, is composed of a material that is inert to water.

2. The gas decomposition apparatus according to claim 1, wherein a voltage source with which a voltage of 1.23 V or higher can be applied is provided.

3. The gas decomposition apparatus according to claim 1, wherein a voltage source with which a voltage of 1.23 V or higher can be applied is provided; the electrolyte is an electrolyte containing water; and, in a state in which a voltage of 1.23 V or higher is applied between the decomposition-side electrode and the counter electrode by using the voltage source, the water in the electrolyte is not decomposed.

4. The gas decomposition apparatus according to claim 1, wherein the decomposition-side electrode is covered with conductive diamond or contains any one of a conductive oxide, a conductive nitride, and a conductive sulfide.

5. The gas decomposition apparatus according to claim 4, wherein the decomposition-side electrode contains Ti4O7 or PbO2.

6. The gas decomposition apparatus according to claim 1, wherein the decomposition-side electrode includes a porous sheet covered with conductive diamond on which Ti4O7 powder and/or PbO2 powder is held.

7. The gas decomposition apparatus according to claim 1, wherein the decomposition-side electrode and the counter electrode have a porosity of 0.6 or more and 0.98 or less, respectively.

8. The gas decomposition apparatus according to claim 1, wherein the electrolyte includes a uniaxially or biaxially stretched porous polytetrafluoroethylene membrane and a perfluorocarbon ion exchange polymer that fills gaps of the porous polytetrafluoroethylene membrane and extends from the catalytic electrode to the counter electrode.

9. The gas decomposition apparatus according to claim 8, wherein a surface of a fiber of the porous polytetrafluoroethylene is covered with a hydrophilic resin film.

10. A method for decomposing a gas, comprising applying a voltage between a decomposition-side electrode and a counter electrode that sandwich an electrolyte therebetween, and introducing gas containing a component to be decomposed through a gas inlet into the decomposition-side electrode to decompose the component,
wherein the decomposition-side electrode contains a material that is inert to water and the electrolyte contains an electrolyte containing water; and
a voltage of 1.23 V or higher is applied between the decomposition-side electrode and the counter electrode so that the component is decomposed without decomposing the water in the electrolyte.

* * * * *